United States Patent
Asai

(10) Patent No.: US 10,517,319 B2
(45) Date of Patent: Dec. 31, 2019

(54) METHOD OF PREPARING MINERAL SUPPLEMENTING AGENT, AND MINERAL SUPPLEMENTING AGENT

(71) Applicants: Shigenori Asai, Shizuoka (JP); Kazumi Ishino, Shizuoka (JP)

(72) Inventor: Shigenori Asai, Shizuoka (JP)

(73) Assignees: Kazumi Ishino, Shizuoka (JP); Shigonori Asai, Shizuoka (JP)

( * ) Notice: Subject to any disclaimer, the term of this patent is extended or adjusted under 35 U.S.C. 154(b) by 0 days.

(21) Appl. No.: 15/565,465

(22) PCT Filed: Mar. 23, 2016

(86) PCT No.: PCT/JP2016/059127
§ 371 (c)(1),
(2) Date: Oct. 10, 2017

(87) PCT Pub. No.: WO2016/163230
PCT Pub. Date: Oct. 13, 2016

(65) Prior Publication Data
US 2018/0125104 A1 May 10, 2018

(30) Foreign Application Priority Data
Apr. 9, 2015 (JP) .................................. 2015-090850

(51) Int. Cl.
*A23L 5/20* (2016.01)
*A23L 19/00* (2016.01)
(Continued)

(52) U.S. Cl.
CPC ........ *A23L 5/23* (2016.08); *A23F 5/36* (2013.01); *A23L 19/01* (2016.08); *A23P 10/00* (2016.08);
(Continued)

(58) Field of Classification Search
CPC ............ A61K 2300/00; A23V 2250/21; A23V 2200/30; A23L 27/88; A23L 5/00;
(Continued)

(56) References Cited

U.S. PATENT DOCUMENTS

2008/0014291 A1   1/2008   Noack

FOREIGN PATENT DOCUMENTS

| CN | 102669462 A | * | 9/2012 | ............... A23K 1/18 |
| JP | 1052240 A | | 2/1998 | |

(Continued)

OTHER PUBLICATIONS

JP 2011-254808 A, Machine English Translation.Published on Dec. 22, 2011 Retrieved online Oct. 15, 2018 translation (Year: 2011).*

(Continued)

*Primary Examiner* — Hong T Yoo
(74) *Attorney, Agent, or Firm* — Browdy and Neimark, PLLC

(57) ABSTRACT

To prepare a mineral supplementing agent capable of commonly used for a seasoning liquid, a supplement, a cosmetic, an oral cavity washing liquid, a plant growth promoting agent and the like, by using common materials and a common preparation method.

A method of preparing a mineral supplementing agent capable of being administered to a human body or a plant is provided. The method includes a first charging step, a second charging step, a third charging step, a fourth charging step, and an extraction step. The first charging step charges a vessel with part of a prescribed amount of vinegar. The second charging step charges the vessel, which has been charged with the vinegar, with at least one of garlic, instant coffee, vinegar, and a fruit. The third charging step charges the vessel, which has been subjected to the second charging step, with at least one of a particulate grain hull, a charred (Continued)

product thereof, and a calcined ash thereof, and mixing the contents of the vessel. The fourth charging step adds the rest of the prescribed amount of vinegar to the vessel which has been subjected to the third charging step, while stirring the contents of the vessel concurrently with the addition. The extraction step separates a liquid component and a solid component in the vessel, after the fourth charging step, and extracts the separated liquid component as a mineral solution.

4 Claims, 25 Drawing Sheets

(51) Int. Cl.
    *A23P 10/00*     (2016.01)
    *A23P 30/00*     (2016.01)
    *A23F 5/36*     (2006.01)
    *C05F 5/00*     (2006.01)

(52) U.S. Cl.
    CPC ............... *A23P 30/00* (2016.08); *C05F 5/002* (2013.01); *A23V 2002/00* (2013.01); *A23V 2250/022* (2013.01); *A23V 2250/212* (2013.01)

(58) Field of Classification Search
    CPC ... A23L 19/01; A23L 7/00; A23L 5/23; A23L 2/52; A23L 33/105; A23L 5/20; A23L 19/00; A23L 7/10; C05F 1/00; C05F 5/002; C05F 5/00; C05G 5/00
    See application file for complete search history.

(56) References Cited

FOREIGN PATENT DOCUMENTS

| | | |
|---|---|---|
| JP | 2005220004 A | 8/2005 |
| JP | 2006271359 A | 10/2006 |
| JP | 2007522101 A | 8/2007 |
| JP | 2007252357 A | 10/2007 |
| JP | 2011254808 A | 12/2011 |
| JP | 2013103126 A | 5/2013 |

OTHER PUBLICATIONS

JP2013-103126 A, Machine English Translation, Published on May 30, 2013 Retrieved online Oct. 15, 2018 translation (Year: 2013).*
CN102669462 A, Abstract English translation, Sep. 19, 2012 (Year: 2012).*

* cited by examiner

FIG. 1

(First step)

Charge vessel with part of prescribed amount of acetic acid (Second step) 

Charge with at least one of garlic, coffee bean, acetic acid, and fruit (Third step) 

Charge with at least one of particulate grain hull, charred product thereof, and calcined ash thereof (Fourth step) 

Mix (Fifth step) 

Stir while adding rest of acetic acid (Sixth step) 

Extract separated liquid component (Seventh step) 

Filter (6'-th step)

Extract separated solid component (7'-th step)

Filter

METHOD OF PREPARING MINERAL SUPPLEMENTING AGENT, AND MINERAL SUPPLEMENTING AGENT

TECHNICAL FIELD

The present invention relates to a mineral supplementing agent. When used for the human body, the mineral supplementing agent of the present invention serves as a seasoning liquid, a brown rice cooking seasoning liquid, a liquid for improving blood circulation, a skin lotion, a liquid for reducing harmful effects of electromagnetic waves or radioactive rays, or an oral cavity washing liquid for use in toothbrushing, gargling, etc. Besides, when used for plant bodies, the mineral supplementing agent of the present invention may be sprayed in a diluted state onto leaf surfaces or near-root portions of crops or may be applied to trunks near roots of fruit trees, thereby serving as a liquid for preventing frost damage to flower buds or for recovering vitality or fertility of trees.

BACKGROUND ART

Conventional seasoning liquids such as soy sauces, sweet sakes (mirin), cooking sakes, broths have been produced mainly by use of foodstuffs. In addition, the brown rice cooking natural seasoning liquid disclosed in JP 2011-254808 A (PTL 2) is produced by use of not only foodstuffs but also shell powder, fine particles of crusts, and/or fine particles of fish bones. However, due to the progress of global environmental pollution nowadays, the demand rather than the supply of the marine organisms and farm products used as the starting materials has increased, leading to scarcity of the starting materials and resulting in a substantial rise in the materials cost of the seasoning liquids and brown rice cooking seasoning liquids. For this reason, while on one hand there are seasoning liquids according to an orientation towards real things in regard of raw material and preparation method, on the other hand many inexpensive seasoning liquids containing many food additives which are questioned about safety for the human body are appearing on the market.

Conventionally, means for improving blood circulation have included pocket warmers, hot-water bottles or bags, poultices, ointments, and internal medicines. However, they differ in use conditions, may need a specialist's diagnosis, and need substantial costs, and few of them are effective for the whole part of the human body. Although the pocket warmer and hot-water bottle or bag disclosed in JP 2013-103126 A (PTL 3) are effective, they are large in volume and bulky to use.

There are innumerable cosmetics and many of them are additive-free cosmetics. However, there are few cosmetics that are tasteless, odorless, non-colored, high in penetrating property, and capable of conditioning the skin.

Besides, a liquid capable of reducing harmful effects of electromagnetic waves and/or radioactive rays has not yet been on the market at present.

There are few tooth powders, liquid dentifrices, or gargles that are produced from only natural materials, and there is found no agent that removes dental plaque, fur on tongue and/or various bacteria on the throat so securely as the agent of the present invention.

Further, in the case of spraying a leaf surface spraying agent or a fertilizer onto plants, generally, no effect can be expected unless the leaf surface spraying agent or fertilizer is sprayed onto leaf surfaces or near-root portions of the crops, and it has been beyond expectation to supply such an agent to a near-root portion of the trunk.

CITATION LIST

Patent Literatures

[PTL 1]
  JP 2005-220004 A
[PTL 2]
  JP 2011-254808 A
[PTL 3]
  JP 2013-103126 A

SUMMARY

Technical Problems

According to the technologies as above, however, there are some problems. If a seasoning liquid is inexpensive though poor in quality, the consumers may purchase the seasoning liquid but they are still anxious about health. When a seasoning liquid is produced using carefully selected raw materials, on the other hand, the seasoning liquid will be high in price and remains as a luxury item for part of the consumers. Thus, security or safety of foods that all people need cannot be ensured. In addition, the pocket warmers, hot-water bottles or bags, poultices, ointments, and internal medicines involve considerable medical expenses and purchase expenses, are bothersome to handle, and they do not make the user really feel that they are effectively functioning as a whole. Further, there is a distinct difference between cosmetics which suit to a user's skin and cosmetics which do not suit to the user's skin; persons with a sensitive skin or with a predisposition to atopy must be careful in selecting cosmetics.

In addition, radioactive substances are still being released from the Fukushima Daiichi Nuclear Power Plant at present, and it is impossible to avoid harmful influences of the radioactive substances even in remote areas. Besides, electromagnetic waves are flying about in the life surrounded with electrical appliances that make the life convenient, and a method for protection against the electromagnetic waves has not come into common use.

The oral cavity washing liquids used for toothbrushing or gargling or the like contain many artificial chemical substances. Although these liquids are effective in whitening the teeth, removing mouth odors, or momentarily removing various bacteria on the throat, therefore, there remains a question about the safety of the chemical substances from the viewpoint of health of the human body as a whole, and there may be a concern about bad influences of the chemical substances on the human body. Thus, the dental plaque, fur on tongue, and various bacteria on the throat are not reduced safely and efficiently.

In addition, although it is practiced to take better care in warming or covering crops in a vinyl plastic hothouse or greenhouse or to construct a tunnel-like vinyl plastic structure, for preventing frost damage, it is necessary to separately give a leaf surface spraying agent or a fertilizer for the purpose of recovering the vitality or fertility of trees. Thus, considerable costs and labor are being taken for such purposes.

According to the present invention, picked fruits such as oranges or ume, grain hulls (e.g., rice hulls or buckwheat hulls), charred product thereof, or calcined ash thereof, which has often been discarded conventionally, is used. By using these 100% natural materials only, mineral components which are commonly difficult to digest and absorb or to use are extracted, to produce a mineral solution. The mineral solution may be used as a seasoning liquid or a brown rice cooking seasoning liquid for eating, may be applied to the human skin for the purpose of improving blood circulation, conditioning the skin, or reducing the harmful effects of electromagnetic waves and/or radioactive rays, or may be used for toothbrushing or gargling. Alternatively, not only the mineral solution but also the remaining solid component may be used as a leaf surface spraying agent or a fertilizer for plants, thereby preventing frost damage to flower buds and/or recovering the vitality or fertility of trees. Thus, it is an object of the present invention to provide a method of preparing a mineral supplementing agent that is useful for human beings, animals, plant bodies, microorganisms in the ground, and small animals in the ground, and also to provide the mineral supplementing agent.

Specifically, it is an object of the present invention to provide a mineral supplementing agent that can be applied to a plurality of uses such as use as a seasoning agent, use as a supplement, and use as a cosmetic, while employing common materials and a common preparation method.

In addition, it is an object of the present invention to provide a mineral supplementing agent that can be prepared through simple steps while using inexpensive materials.

Further, it is an object of the present invention to prepare a highly safe mineral supplementing agent by using inedible parts of vegetables, fruits and other foodstuffs which have conventionally been disposed of, and by extracting effective ingredients efficiently.

Solution to Problems

A method of preparing a mineral supplementing agent of the present invention is (1) a method of preparing a mineral supplementing agent capable of being administered to a human body or a plant, the method characterized by including a first charging step, a second charging step, a third charging step, a fourth charging step, and an extraction step. The first charging step charges a vessel with part of a prescribed amount of vinegar. The second charging step charges the vessel, which has been charged with the vinegar, with at least one of garlic, instant coffee, vinegar, and a fruit. The third charging step charges the vessel, which has been subjected to the second charging step, with at least one of a particulate grain hull, a charred product thereof, and a calcined ash thereof, and mixes the contents of the vessel. The fourth charging step adds the rest of the prescribed amount of vinegar to the vessel which has been subjected to the third charging step, while stirring the contents of the vessel concurrently with the addition. The extraction step separates a liquid component and a solid component in the vessel, after the fourth charging step, and extracts the separated liquid component as a mineral solution.

In addition, in the method of preparing a mineral supplementing agent of the present invention, it is preferable that (2) at least one of the garlic in a powdery form, the instant coffee in a powdery form, the vinegar in a powdery form, and a dried powder of a juice of the fruit is used in the second charging step.

In the method of preparing a mineral supplementing agent of the present invention, it is preferable that (3) the method further includes a distillation step of further distilling the mineral solution extracted in the extraction step, to produce a substantially tasteless, odorless, and non-colored solution.

Further, in the method of preparing a mineral supplementing agent of the present invention, it is preferable that (4) the method further includes a residue extraction step of extracting the solid component left upon the extraction step, for use as a fertilizer for plants.

A mineral supplementing agent of the present invention is (5) characterized by including vinegar, at least one of garlic powdered to nanometer order, instant coffee powdered to nanometer order, vinegar powdered to nanometer order, and a dried powder of a juice of a fruit, and at least one of a nanometer-order particulate grain hull, a charred product thereof, and a calcined ash thereof.

In addition, the mineral supplementing agent of the present invention in the (5) above, which preferably (6) contains, mixed therein all of the garlic powdered to nanometer order, the instant coffee powdered to nanometer order, the vinegar powdered to nanometer order, and the dried powder of the juice of the fruit, and further, all of the particulate grain hull, the charred product thereof, and the calcined ash thereof.

Advantageous Effects of Invention

According to the present invention, a mineral supplementing agent capable of being used in common as a seasoning liquid, a supplement, a cosmetic, an oral cavity washing liquid, a plant growth promoting agent and the like can be prepared using common materials and a common preparation method.

In addition, according to the present invention, first, a preparation tank is charged with approximately 25% of a total amount of vinegar to be used. Any one or more of garlic powder, instant coffee, a powder of freeze-dried vinegar, and a juice of a picked fruit such as orange or ume are dissolved into the vinegar in the tank, to produce a highly viscous acidic solution. This ensures that dissolution of grain hulls which are basic (e.g., rice hulls or buckwheat hulls), a finely crushed product thereof, a charred product thereof, or a calcined ash thereof proceeds efficiently, generation of foams or bubbles is restrained due to the high viscosity, and the capacity of the preparation tank can be minimized. Thereafter, the contents of the tank are stirred while gradually adding the remaining approximately 75% of the total amount of vinegar thereto. Thus, although some labor is needed for filtration of the seasoning liquid and dregs, a mineral solution of high quality can be prepared most stably and in a short time.

Besides, a first one of the advantageous effects of the present invention is that a mineral solution suited to various uses can be produced using limited starting materials such as garlic powder, instant coffee, a powder of freeze-dried vinegar, a juice of a picked fruit such as orange or ume, grain hulls (e.g., rice hulls or buckwheat hulls), finely crushed grain hulls, a charred product thereof, or a calcined ash thereof. The picked fruits such as oranges and ume, grain hulls (e.g., rice hulls and buckwheat hulls), a charred product thereof, and a calcined ash thereof, which are ordinarily disposed of without being used as food or as materials for making daily goods, are positively used in the present invention. Due to changes in the ecosystem arising from worsening of global environments and unseasonable weather, the kinds and amounts of resources in the ocean and on land which can be utilized by the human beings have been decreasing. In such a situation, it is an excellent countermeasure against the difficulty of obtaining food and against the worsening of environments to be able to produce a mineral solution useful for the human beings through effective use of these conventionally buried resources.

A second one of the advantageous effects of the present invention is that an excellent seasoning liquid and an excellent brown rice cooking seasoning liquid can be prepared. The brown rice cooking seasoning liquid introduced by PTL 2 is produced using marine resources such as shell powder, fine particles of crusts, and fine particles of fish bones. According to the present invention, even when these marine resources are reduced in amount, a similar seasoning liquid and a similar brown rice cooking seasoning liquid can be prepared using the grain hulls which are removed from large amounts of grains produced throughout the world. The grain hulls can be secured more stable than the marine resources and can be obtained for almost nothing. In addition, the quality of the seasoning liquid and the brown rice cooking seasoning liquid has been improved as compared with the brown rice cooking seasoning liquid disclosed in Citation List. The brown rice cooking seasoning liquid prepared by using instant coffee, garlic powder, and vinegar together with the grain hulls adopted in place of the shell hulls, fine particles of crusts, and fine particles of fish bones has little odor as compared to the brown rice cooking seasoning liquid of Citation List, is cooked to be cooked brown rice having a white shade near that of cooked polished rice, being soft and easy to eat. Moreover, the taste of the cooked brown rice compares favorably with the taste of cooked polished rice.

A third one of the advantageous effects of the present invention is that the single mineral solution can serve as solutions for different uses, including a seasoning liquid, a brown rice cooking seasoning liquid, a liquid for improving blood circulation, a liquid for reducing harmful influences of electromagnetic waves and/or radioactive rays, and an oral cavity washing liquid for use in toothbrushing, gargling or the like. In other words, when the mineral solution prepared from the mineral supplementing agent of the present invention is taken into the human body as food, minerals and calcium which are essential elements for the living body can be promptly absorbed as nutrients. When the mineral solution is applied to an aching part, a cold part, or a bad-conditioned part of the body, blood circulation is improved and the cold, ache, or the bad condition of the body can be alleviated. In addition, the minerals and calcium absorbed through the skin in high concentrations reduce the harmful influences of electromagnetic waves and/or radioactive rays. When the mineral solution is used in the mouth as a liquid dentifrice or gargling liquid, the environments in the oral cavity can be kept healthy.

Besides, according to the present invention, when the mineral solution is further subjected to distillation, the resulting mineral solution is a nearly tasteless, odorless, and non-colored transparent solution. The transparent solution is suitable for use as a cosmetic, and satisfies the modern people's taste of disliking odor and coloration. Further, the solution becomes a mineral supplementing agent for the human body that is highly penetrating into the skin and agrees with the skin without growing sticky.

In addition, the liquid component and the dregs in the present invention and the liquid component containing the pasty solid component remaining upon distillation in the present invention may each be diluted with water to produce a leaf surface spraying agent, which may be sprayed onto leaf surfaces or near-root portions of crops. Alternatively, the undiluted solution and the dregs may each be used as a fertilizer, which may be applied to near-root portions of the trunks of fruit trees. By these operations, it is possible to prevent frost damage to flower buds, to recover the vitality or fertility of trees, to make fruits grow to be firm and/or large, to promote ripe coloration of fruits or vegetables, and to enhance umami and sugar content. By use of the mineral solution which thus has a multiplicity of efficacies while being a single material, the user can realize a reduction in cost, enhance working efficiency, and harvest high-quality crops over a long period of time. In addition, by using the mineral solution as a fertilizer, microorganisms in the ground and small animals in the ground are activated, whereby environments for growth of plants are conditioned, and gardening in facilities, raising plants outdoors, and fruit growing that do not exert a burden on the global environments can be realized.

Each of the subject matters of the present invention can exhibit a variety of advantageous effects on the living bodies because the mineral supplementing agent becomes a mineral solution that contains ultrafine particulate (nanometer-sized) minerals, calcium, and neutralized organic acid. Specifically, by a combination of an acidic substance and a basic substance in the starting materials derived from organic matters which are natural matters not containing any artificial chemical substances, an acid-base chemical reaction takes place in a natural form. As a result, the minerals and calcium in the grain hulls, charred product thereof, or calcined ash thereof being difficult to decompose is converted into ultrafine particulates (nanometer-sized) and dissolved and eluted in the solution together with the neutralized organic acid. Therefore, the ultrafine particulate (nanometer-sized) minerals, calcium, and neutralized organic acid act effectively on not only the human body but also animals, plant bodies, microorganisms in the ground, and small animals in the ground. Besides, even when used in large amounts in the plant growth environments, the mineral solution does not exert a burden on the ecosystem and does not cause environmental destruction.

The ultrafine particulate (nanometer-sized) minerals, calcium, and neutralized organic acid produced by the combination of organic matters are stabilized in shape for a long time, and can continue acting usefully for a long time even after taken into the living body as the good-quality minerals, calcium, and neutralized organic acid.

For example, when the mineral solution of the present invention is used as a seasoning liquid in making a side dish, the ultrafine particulate (nanometer-sized) minerals, calcium, and neutralized organic acid increase the nutritional value of the food such as vegetables, meat, and fish, and improve transfer of heat through the food. As a result, the heating time can be shortened, and the cooked side dish and cooked brown rice can be eaten with a feeling of better taste. In the body, further, they act as minerals, calcium, and neutralized organic acid which are high in absorbance and can be utilized promptly, thereby conditioning the environments in the living body, and are transported as nutrients to various parts of the body, thereby functioning effectively there.

For instance, when the mineral solution of the present invention is used in cooking of brown rice as a brown rice cooking seasoning liquid, heat absorptivity within the pan or cooker is enhanced by the ultrafine particulate (nanometer-sized) minerals, calcium, and neutralized organic acid. Therefore, water penetrates into the brown rice by breaking the hard hull at the surface of the brown rice, whereby soft cooked brown rice easy to eat can be readily obtained.

Specifically, when the mineral solution of the present invention is added in an amount of 5 cc per 1 go (approximately 180 cc) of brown rice at the time of cooking brown rice, and water is used in an amount greater than an ordinarily prescribed amount by 80 cc to 100 cc per 1 go of brown rice, soft cooked brown rice tasting good can be obtained under the functions of the ultrafine particulate (nanometer-sized) minerals, calcium, and neutralized organic acid, even when cooking of the brown rice is started immediately without any time taken for absorption of water into the brown rice. Thus, labor and time for cooking brown rice are saved, whereby more people can be helped to be familiar with and normally eat cooked brown rice at tables. Besides, the nutritional value of the mineral solution of the present invention is added to the nutritional value possessed by cooked brown rice, so that digestion and absorption of the cooked brown rice can be assisted, and this serves for making the cooked brown rice a complete food. Further, since brown rice contains a large amount of phytic acid having the function of discharging harmful substances and radioactive substances out of the body, the synergistic effect thereof promotes the change of the human body to a more healthy state by eating the cooked brown rice, and an eating habit suitable for augmenting health can be taken naturally. Moreover, it is the greatest advantage of the present invention to make it possible to produce and supply the inexpensive high-quality brown rice cooking seasoning liquid, while using as a main starting material the grain hulls which are extremely abundant upon harvest.

Nowadays, a phenomenon in which a plant body takes in cesium by mistaking it for potassium and takes in strontium by mistaking it for calcium has been reported many times. In the mineral supplementing agent of the present invention, a calcined ash of grain hulls is used as a starting material. The calcined ash contains large amounts of minerals (such as potassium) and calcium. Potassium is a substance similar to cesium which is a radioactive substance, and calcium is a substance similar to strontium which is a radioactive substance. When the mineral solution of the present invention is applied to a human body or the undiluted solution is directly sprayed onto a near-root portion of the trunk of a tree (plant body), therefore, it is possible to inhibit the radioactive cesium or strontium from being taken into the living body, and to reduce harmful influences of the radioactive substance.

In the modern society, we are surrounded by electrical appliances very closely. The use of a smartphone, mobile phone, or tablet personal computer (PC) for a long period has come to often keep the human body in the same posture for a long time. As a result, a muscle of the body may be hardened, poor blood circulation may be brought about, and the body may be stiffened. In the range from optic nerves to peripheral nerves, fatigue may occur in each muscle and inside the brain. When the mineral solution of the present invention is applied to the stiffened part of the human body, for example, the neck, the shoulder, the back, or the tip of a hand or foot, the particulate (nanometer-sized) minerals, calcium, and neutralized organic acid are absorbed into the body through the skin, to promote metabolism and blood circulation in the relevant part of the body, thereby alleviating the stiff of the body.

In addition, when the mineral solution of the present invention is similarly applied to a cold part of the human body, for example, the shoulder, the back, or the tips of hands or feet, it is possible to promote metabolism and improve blood circulation in the relevant part of the body, whereby the cold of the body is gradually improved. Further, when a small amount of the mineral solution of the present invention is periodically applied to an aching part, a bad-conditioned part, or a parietal region of the human body, it is possible to promote metabolism and blood circulation in the relevant part of the body, whereby the ache or bad condition of the body is gradually mitigated. When a small amount of the undiluted solution is applied to each part of the human body, the particulate (nanometer-sized) minerals, calcium, and neutralized organic acid are absorbed into the body through the skin, to serve for making the human body normal and steady.

For example, when the mineral solution of the present invention is used as an oral cavity washing liquid in tooth-brushing or gargling, the persistent contaminants in the oral cavity such as dental plaque and fur on tongue as well as various bacteria adhering on the oral cavity parts or the throat can be washed or shaved off by the ultrafine particulate (nanometer-sized) minerals, calcium, and neutralized organic acid owing to the fineness of them. Moreover, the liquid dentifrice and the gargling liquid do not have any side effect.

Further, when the mineral solution of the present invention is used for a plant body, the danger that the plant body thus treated might absorb the radioactive cesium or strontium by mistake is reduced by the ultrafine particulate (nanometer-sized) minerals, calcium, and neutralized organic acid. In the case where a calcined ash of grain hulls is used as a starting material, potash as one of the fertilizer components indispensable to growth of plant bodies (namely, nitrogen, phosphoric acid, and potash) can be taken into the plant body in a large amount, whereby firm rooting of the plant is ensured and the plant's ability of making flowers and fruits is enhanced. Also, the activities of microorganisms in the ground and small animals in the ground existing in the fertilized soil are activated, to positively act on the growth environments for the plant body, thereby assisting the growth of the plant.

When the mineral solution of the present invention is further subjected to distillation and the resulting solution is used as a skin lotion, the fineness of the ultrafine particulate (nanometer-sized) minerals, calcium, and neutralized organic acid is increased, though the amounts of the ultrafine particulate (nanometer-sized) minerals, calcium, and neutralized organic acid are reduced through the distillation process. As a result, the penetrating property of the mineral solution to the skin texture of the human body is markedly increased, helping to obtain a smoother skin. Thus, a high-quality skin-care products and cosmetics can be produced.

BRIEF DESCRIPTION OF DRAWINGS

FIG. 1 is a flow chart depicting a method of preparing a mineral supplementing agent according to a first embodiment of the present invention.

DESCRIPTION OF EMBODIMENTS

Figure 2:
FIG. 2 is a flow chart depicting a method of preparing a mineral supplementing agent according to a second embodiment of the present invention.

An embodiment for carrying out the present invention will be described below. Note that while a method of preparing a mineral supplementing agent of the present invention will be described in an exemplifying manner in each of the drawings and the following description, the description naturally is not limitative of the technical scope of the invention. In addition, to other configurations than the configuration particularly detailed below, known configurations and/or structures such as those described, for example, in PTLs 1 to 3 may be applied as required.

First Embodiment

<Method of Preparing Mineral Supplementing Agent for Living Body>

FIG. 1 is a flow chart depicting a method of preparing a mineral supplementing agent for a living body according to a first embodiment of the present invention.

In preparing the mineral supplementing agent of the present embodiment, first, a vessel such as a tank is charged with a partial amount of vinegar, namely, part of an amount of vinegar to be used (first charging step: first step).

The amount of vinegar with which the vessel is charged in the first step is preferably a partial amount, namely, part of the total amount (prescribed amount) of vinegar, which is the sum of the partial amount and the amount of vinegar to be used in a later fifth step. The partial amount is preferably an amount of ⅓, ¼ or the like fraction of the total amount (prescribed amount).

Note that the vinegar used in the first step is preferably a liquid vinegar, for enabling exudation of components of each of substances with which the vessel will be charged in later steps. In addition, as the vinegar used in the first step, there is preferably used brewed vinegar, grain vinegar, or rice vinegar ordinarily used as food, but there may also be used wine vinegar, balsamic vinegar, cider vinegar, ume vinegar, persimmon vinegar and the like.

Next, the vessel charged with vinegar in the first step is subsequently charged with at least one of garlic, instant coffee, vinegar, and a fruit (second charging step: second step). After the charging, stirring is preferably conducted until each of this-time materials make contact with the vinegar with which the vessel was charged in the first step.

The material or materials with which the vessel is charged in the second step are preferably powdery or pasty, in order to permit exudation of components thereof. Specifically, as garlic, garlic pulverized into a powdery form after freeze drying or a material obtained by crushing raw garlic into a pasty form is preferably used. As instant coffee, a powder obtained by drying a coffee extract liquid is preferably used.

As vinegar with which the vessel is charged in the second step, a powdery material obtained by pulverizing freeze-dried vinegar is preferably used.

As the fruit, a powdery material obtained by freeze drying a fruit juice or the like and then pulverizing the dried juice or a pasty material obtained by smashing a raw fruit is preferably used. The fruit to be used is preferably of the kind that contains an organic acid (citric acid, tartaric acid, malic acid, or succinic acid), for example, citrus fruits such as satsuma mandarin (Citrus unshu), lemon, citrus junos, other examples including apple, pear, persimmon, and ume.

Subsequently, the vessel is charged with at least one of a particulate grain hull, a charred product thereof, and a calcined ash thereof (third charging step: third step). After the charging, stirring is preferably conducted until each of this-time materials make contact with the vinegar with which the vessel was charged with in the first step and each of the materials with which the vessel was charged in the second step.

Examples of the grain hull with which the vessel is charged in the third step include rice hulls. The grain hulls are used in the present invention, since grain hulls are available continuously and inexpensively, and can serve as a source of water-soluble calcium and water-soluble minerals through an acid-base reaction.

The grain hull to be used in the present invention may be a material obtained from grain hulls by firing or baking (e.g., smoked rice hulls). Besides, the grain hull to be used in the present invention may be a charred product.

The grain hull may be pulverized into a particulate form, before charging. The particulate form in the present invention is preferably a form of particulates having a size of 1 μm to 100 μm, for example, which is not limitative.

Note that a shell powder, fine particles of crust, or fine particles of fish bone may be added in the second step or the third step above. In this case, the finished mineral supplementing agent has an enhanced calcium content, which is preferable.

Besides, herbs such as clove, sage, peppermint, and cinnamon may be added in the second step or the third step above. In this case, the finished mineral supplementing agent has the herb's scent added thereto, and the finished mineral supplementing agent has a shelf life prolonged due to the disinfecting effect of the herb, which is preferable.

After the vessel is charged with at least one of the particulate grain hull, the charred product thereof, and the calcined ash thereof in the third step, the resulting mixture in the vessel is preferably stirred and mixed sufficiently (fourth step). The grain hull, charred product thereof, or the calcined product thereof with which the vessel is charged in the third step preferably has a basic (alkaline) property. In this case, by the mixing in the fourth step, the acidic substances with which the vessel was charged in the first step and the second step and the basic substance or substances with which the vessel was charged in the third step perform an acid-base chemical reaction. By the chemical reaction, calcium carbonate contained in a large amount in the grain hull, charred product thereof, or calcined product thereof with which the vessel was charged in the third step is softened and decomposed, to produce carbon dioxide gas.

After the generation of the carbon dioxide gas subsides, the vessel is charged with vinegar (fourth charging step: fifth step). The amount of vinegar added at this stage is the remaining amount obtained by subtracting the partial amount of vinegar added in the first step from the total amount of vinegar. At this stage, the vinegar with which the preparation tank is to be charged may be added at a time, but it is preferable that the charging operation may be divided into a plurality of divisional operations. When the charging with vinegar is conducted by a plurality of divisional operations, the contact between the vinegar and the other substances takes place more easily.

Before and after the charging with vinegar in the fifth step, stirring is conducted to cause contact between the vinegar and the other substances. Particularly, the mixture as a whole is stirred until the grain hull or calcined ash thereof with which the vessel is charged in the third step absorbs sufficiently the liquid vinegar added in the first step or the fifth step.

When this mixture is let stand, the solid component sediments to the bottom of the preparation tank under gravity. The time for which the mixture is let stand is not particularly limited, and is preferably approximately six hours to five days.

The liquid component separated is taken out (extraction step: sixth step). The method for taking out (extracting) the liquid component is not specifically restricted, and the supernatant liquid may be taken out by inclining the preparation tank. Alternatively, the supernatant liquid may be ladle out by a vessel or drawn by a pump.

The liquid component thus extracted is filtered through a filter paper if necessary (seventh step). Through this filtration step, a liquid free of precipitate can be obtained. The filtration may be repeated a plurality of times, as required. Note that the seventh step is not an indispensable step, and may be conducted according to the use.

The liquid obtained upon the sixth step or the seventh step above is made to be a mineral supplementing agent for the living body. Note that since the liquid obtained in the present embodiment is in the form that enables easy taking into the body, the liquid has been described as a mineral supplementing agent for the living body, for convenience. However, the use of the liquid is not necessarily limited to the use for the living body; the liquid obtained may be used as a mineral supplementing agent for plants, depending on the mode of use thereof.

The mineral supplementing agent obtained as above can be used, for example, as a brown rice cooking seasoning liquid. The mineral supplementing agent is used by a method wherein at the time of cooking brown rice, water is used in an amount greater than an ordinary prescribed amount by 80 cc to 100 cc per 1 go of brown rice, and, further, the mineral supplementing agent obtained in the present embodiment is added in an amount of approximately 5 cc per 1 go of brown rice, before cooking. The cooked brown rice obtained by cooking in this manner is soft in the cooked state and good in taste and tenderness to the tooth, as compared with the cooked brown rice obtained upon cooking without addition of the mineral supplementing agent of the present invention.

Second Embodiment

<Method of Preparing Mineral Supplementing Agent for Plants>

Now, as a second embodiment of the present invention, a method of preparing a mineral supplementing agent for plants will be described below. FIG. 2 is a flow chart depicting a method of preparing a mineral supplementing agent for plants according to the second embodiment of the present invention. Note that first to fifth steps of the preparation method in the second embodiment are the same as the first to fifth steps in the first embodiment, and, therefore, descriptions of these steps are omitted here, and the process from the end of the fifth step will be described.

After the fifth step in the first embodiment is finished, the solid component (residue) is taken out (residue extraction step: 6'-th step).

In extracting the solid component (residue), it is recommendable that the residue left upon the extraction of the liquid component in the sixth step in the first embodiment is directly made to be the solid component (residue) in the 6'-th step. Since the solid component (residue) thus taken out contains mixed therein the remaining portion of the liquid component in the above-described sixth step, the solid component (residue) is in a non-dried state, but it can be used as it is as a mineral supplementing agent for plants.

Note that it is possible, if necessary, to filter the solid component (residue) in the 6'-th step to remove the liquid component (7'-th step), and to use the resulting matter as a mineral supplementing agent for plants. Note that the 7'-th step is not an indispensable step, and may be conducted according to the use.

The mineral supplementing agent for plants obtained as above can be used, for example, by directly applying it as it is to the trunk of a plant as a fertilizer, or by placing it in or on soil as a plant fertilizer.

Note that while the solid component obtained in the present embodiment has been described as a mineral supplementing agent for plants for convenience, the use of the mineral supplementing agent is not limited to the use for plants; thus, the solid component may be used as a mineral supplementing agent for the living body, depending on the mode of use thereof.

<<First Modification>>

Now, a modification of the first embodiment of the present invention will be described below. While the liquid component has been filtered to obtain a mineral supplementing agent for the living body in the first embodiment above, the liquid component upon filtration can be further subjected to distillation before use (distillation step). Such distillation can be carried out by a known method.

The liquid obtained by the distillation is suppressed in odor of vinegar, as compared with the liquid before the distillation, and is nearly odorless; when the liquid is used as food, therefore, the liquid does not change the tastes of other foods. In addition, since odor is suppressed by the distillation, the liquid can be used by being applied to the skin as a skin lotion, which is preferable.

<<Second Modification>>

A modification of the second embodiment of the present invention will be described. While the solid component obtained from a mixture by separation has been used as a mineral supplementing agent for plants in the second embodiment above, it is possible to dry the solid component, process the dried solid component into a powdery form or a tablet form, and to use the powder or tablets as a mineral supplementing agent for plants. Note that the drying can be performed by a known method. For example, natural drying in the atmospheric air may be adopted, or firing at a low temperature in an oven may be adopted. In addition, drying by a freeze drying method can also be performed.

Like in the second embodiment above, the dried mineral supplementing agent can be used by placing it on or in soil as a plant fertilizer, or can be used by mixing it into soil as a soil improving agent or a soil modifying agent.

EXAMPLES

Example 1

Figure 3:
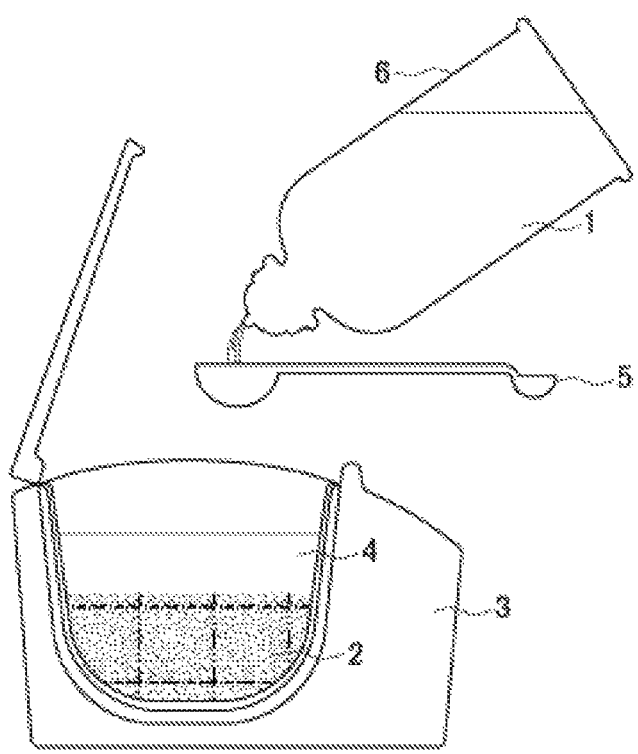
FIG. 3 is a sectional view depicting an embodiment of the present invention.
Figure 4:
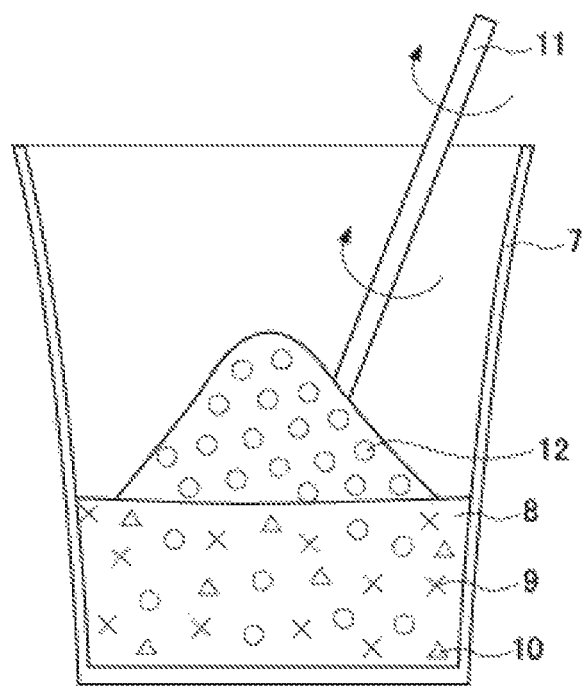
FIG. 4 is a sectional view depicting a preparation process of the present invention.
Figure 5:
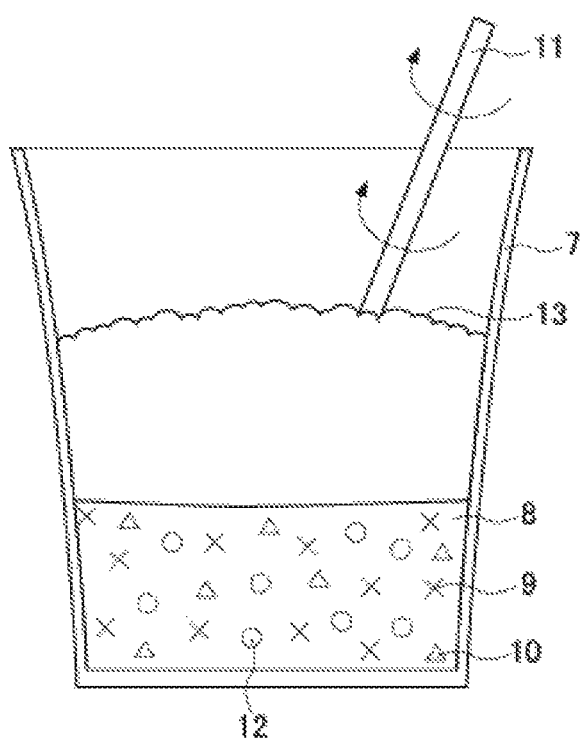
FIG. 5 is a sectional view depicting the preparation process of the present invention.

FIG. 3 illustrates a case in which a mineral supplementing agent for the living body depicted in the present invention serves as 1 (brown rice cooking seasoning liquid). A preparation method of the first-named invention is as illustrated in FIGS. 4 to 7. As depicted in FIG. 4, 7 (preparation tank) is charged with 40 L of 8 (vinegar), and then immediately with 20 kg of 9 (garlic powder) and 5 kg of 10 (instant coffee), and followed by stirring well. Thereafter, 40 kg of 12 (fine particles of rice hulls) is placed in 7 (preparation tank), and the contents are again mixed well. As a result, 12 (fine particles of rice hulls) which is basic undergoes an acid-base chemical reaction with 9 (garlic powder), 10 (instant coffee), and 8 (vinegar) which are acidic, and calcium carbonate contained in a large amount in 12 (fine particles of rice hulls) is softened and decomposed. Then, carbonic acid is released from 12 (fine particles of rice hulls), 13 (bubbles of a mixture generated upon mixing together of the fine particles of rice hulls, the garlic powder, the instant coffee, and vinegar) is rapidly generated, and the solution is expanded, as depicted in FIG. 3. Although the chemical reaction in this instance is rapid and vigorous, it becomes calm in a short time, since stirring has preliminarily been conducted well.

Figure 6:
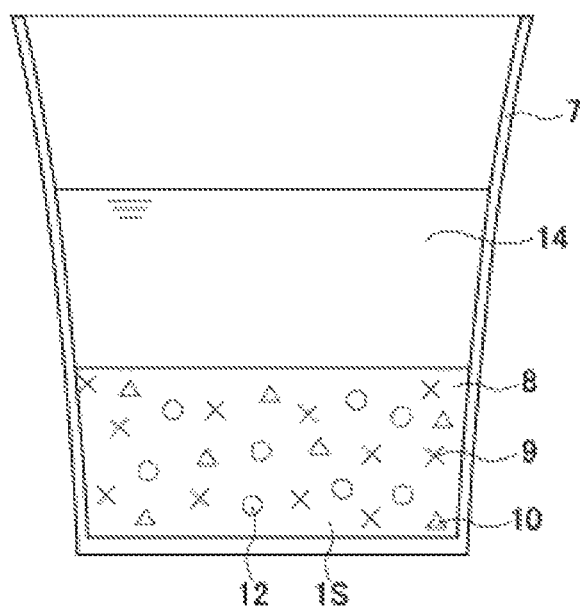
FIG. 6 is a sectional view depicting the preparation process of the present invention.
Figure 7:
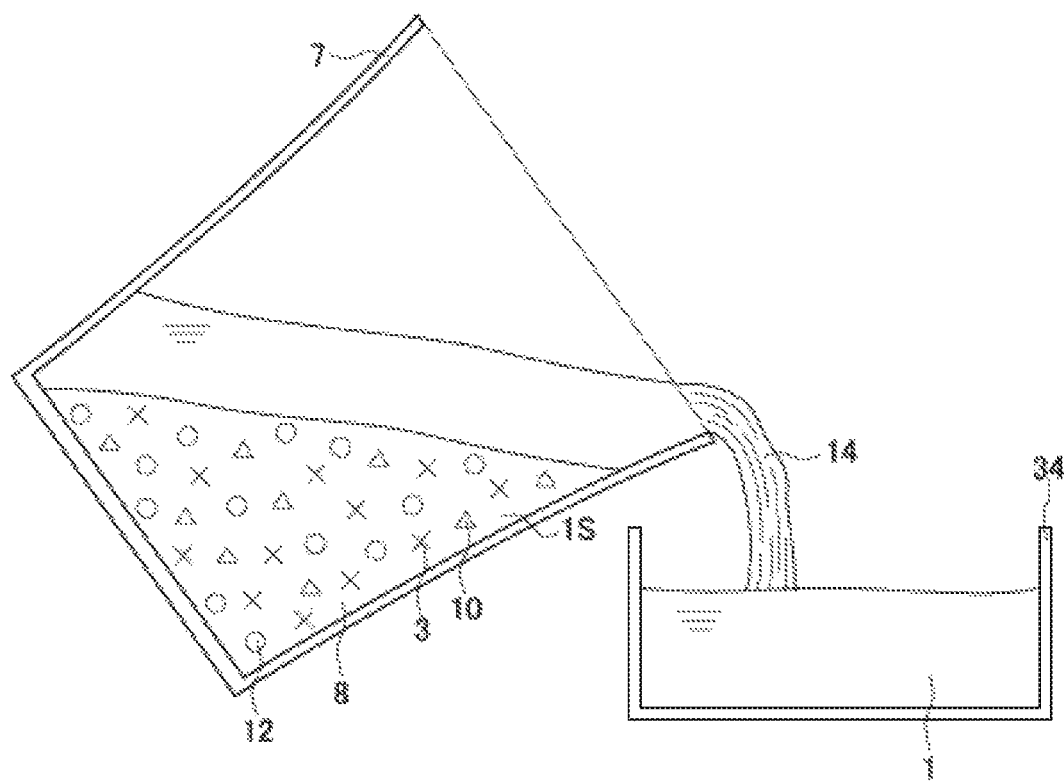
FIG. 7 is a sectional view depicting the preparation process of the present invention.

Thereafter, also, 40 L each of 8 (vinegar) is placed into 7 (preparation tank) three times. In this case, an operation of pouring 8 (vinegar) and stirring the contents well when the previous chemical reaction and the rapid bubbling have subsided is repeated. After a total of 120 L of 8 (vinegar) is entirely poured into 7 (preparation tank) and the contents therein were stirred, the contents are left to stand for one day. As a result, as depicted in FIG. 6, liquid component 14 (mineral solution to be used for the living body) and solid component 15 (dregs containing a mineral solution after making of the mineral solution to be used for the living body) are separated within 7 (preparation tank). As depicted in FIG. 7, this 7 (preparation tank) is inclined obliquely, only supernatant liquid component 14 (mineral solution to be used for the living body) is simply filtered, in such a manner that pasty solid component 15 (dregs containing the seasoning liquid after making of the mineral solution to be used for the living body) in the bottom does not mix in, to be used as 1 (brown rice cooking seasoning liquid). Further, the rough solid component 15 (dregs containing the mineral solution after making of the mineral solution to be used for the living body) in the bottom is also securely filtered, to use 1 (brown rice cooking seasoning liquid) as much as possible.

As depicted in FIG. 3, 3 (rice cooker) is charged with 2 (brown rice) lightly washed with water, 4 (water) in an amount necessary for rice cooking, namely, an amount prescribed for a brown rice course by each rice cooker maker, plus an additional amount of 80 cc to 100 cc per 1 go of brown rice, and thereafter with 1 (brown rice cooking seasoning liquid) (prepared in such a manner above) in an amount of 5 cc per 1 go of 2 (brown rice), immediately followed by starting the rice cooking. The cooked brown rice cooked by use of 1 (brown rice cooking seasoning liquid) tastes good, is free of odor of garlic, has a whitish hue, and resembles cooked polished rice.

Example 2

Figure 8:
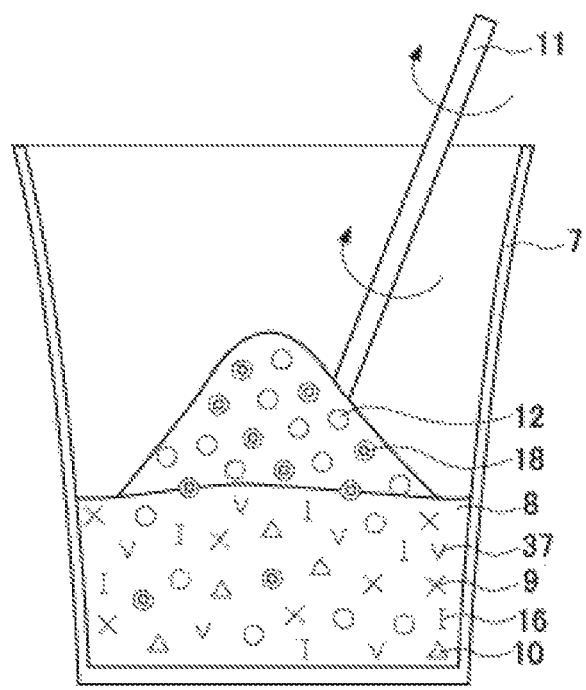
FIG. 8 is a sectional view depicting the preparation process of the present invention.
Figure 9:
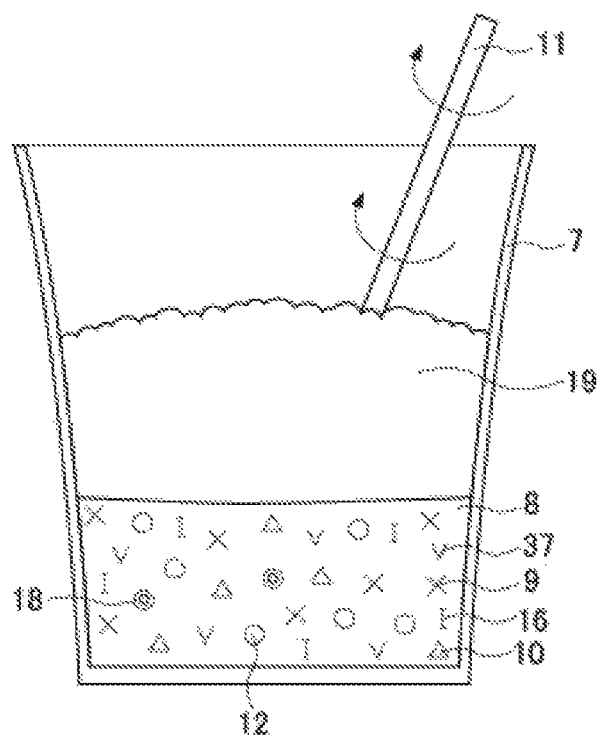
FIG. 9 is a sectional view depicting the preparation process of the present invention.

Another preparation method for 1 (brown rice cooking seasoning liquid) will be described below. A preparation method illustrated in FIGS. 8 to 11 is as follows. As depicted in FIG. 8, 7 (preparation tank) is charged with 40 L of 8 (vinegar), and then immediately with 20 kg of 9 (garlic powder), 5 kg of 10 (instant coffee), 5 kg of 16 (powder of freeze-dried vinegar), and 5 kg of 17 (extract obtained by processing orange fruit into a pasty form), followed by stirring the contents well. Thereafter, 7 (preparation tank) is charged with 20 kg of 18 (calcined ash of rice hulls) and 20 kg of 12 (fine particles of rice hulls), followed again by mixing the contents well. As a result, 18 (calcined ash of rice hulls) and 12 (fine particles of rice hulls) which are basic undergo an acid-base chemical reaction with 9 (garlic powder), 10 (instant coffee), 16 (powder of freeze-dried vinegar), 17 (extract obtained by processing orange fruit into a pasty form), and 8 (vinegar) which are acidic, and calcium carbonate contained in large amounts in 18 (calcined ash of rice hulls) and 12 (fine particles of rice hulls) is softened and decomposed. Then, carbonic acid is released from 18 (calcined ash of rice hulls) and 12 (fine particles of rice hulls), 19 (bubbles of a mixture generated upon mixing together of the calcined ash of rice hulls, the fine particles of rice hulls, the garlic powder, the instant coffee, the powder of freeze-dried vinegar, the extract obtained by processing orange fruit into a pasty form, and vinegar) is rapidly generated, and the solution is expanded, as depicted in FIG. 9. Although the chemical reaction in this instance is rapid and vigorous, it becomes calm in a short time, since stirring has preliminarily been conducted well.

Figure 10:
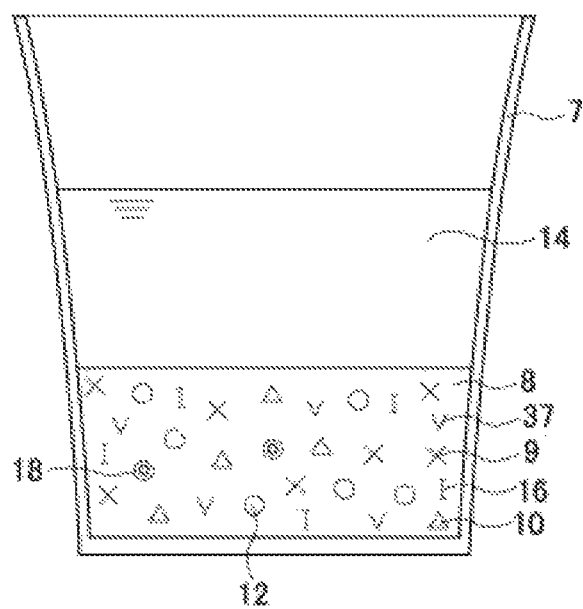
FIG. 10 is a sectional view depicting the preparation process of the present invention.
Figure 11:
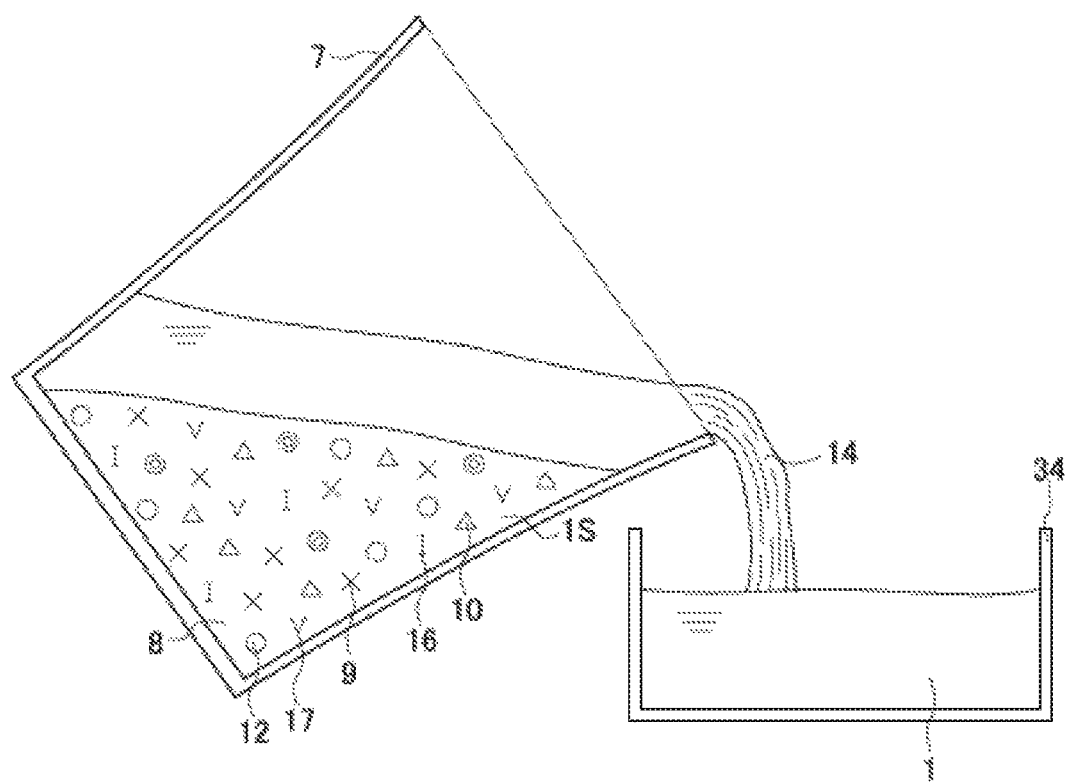
FIG. 11 is a plan view depicting the preparation process of the present invention.

Thereafter, also, 40 L each of 8 (vinegar) is placed into 7 (preparation tank) three times. In this case, an operation of pouring 8 (vinegar) and stirring the contents well when the previous chemical reaction and the rapid bubbling have subsided is repeated. After a total of 120 L of 8 (vinegar) is entirely poured into 7 (preparation tank) and the contents therein are stirred, the contents are left to stand for approximately 12 hours. As result, as depicted in FIG. 10, liquid component 14 (mineral solution to be used for the living body) and solid component 15 (dregs containing a mineral solution after making of the mineral solution to be used for the living body) are separated within 7 (preparation tank). As depicted in FIG. 11, this 7 (preparation tank) is inclined obliquely, only supernatant liquid component 14 (mineral solution to be used for the living body) is simply filtered, in such a manner that pasty solid component 15 (dregs containing the seasoning liquid after making of the mineral solution to be used for the living body) in the bottom does not mix in, to be used as 1 (brown rice cooking seasoning liquid). Further, the rough solid component 15 (dregs containing the mineral solution after making of the mineral solution to be used for the living body) in the bottom is also securely filtered, to use 1 (brown rice cooking seasoning liquid) as much as possible.

As depicted in FIG. 3, 3 (rice cooker) is charged with 2 (brown rice) lightly washed with water, 4 (water) in an amount necessary for rice cooking, namely, an amount prescribed for a brown rice course by each rice cooker maker, plus an additional amount of 80 cc to 100 cc per 1 go of brown rice, and thereafter with 1 (brown rice cooking seasoning liquid) (prepared in such a manner above) in an amount of 5 cc per 1 go of 2 (brown rice), immediately followed by starting the rice cooking.

The 1 (brown rice cooking seasoning liquid) depicted in FIG. 3 can be used not only for brown rice cooking but also for making side dishes. When 1 (brown rice cooking seasoning liquid) is used in combination with other seasonings as a seasoning or flavoring for boiled food, a grilled dish, or a noodle dipping sauce, in the same manner as the existing seasonings such as soy sauce, cooking sake, sweet sake (mirin), and sugar, it is possible to give a garlic flavor and to strengthen nutritional components. In addition, a shortening of cooking time can be realized.

Example 3

Figure 12:
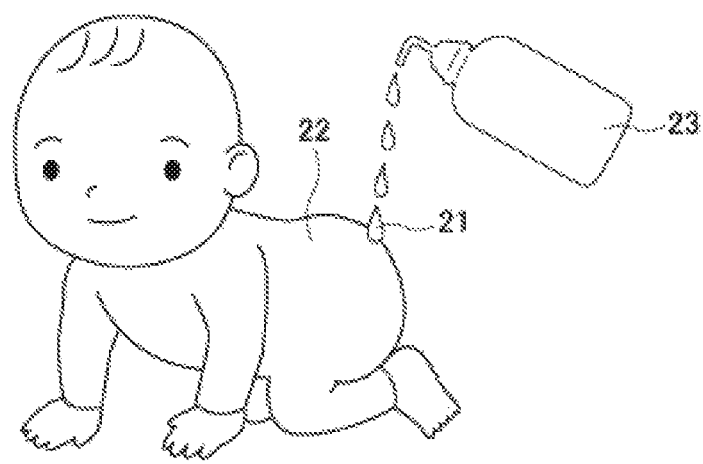
FIG. 12 is a plan view depicting an embodiment of the present invention.
Figure 13:
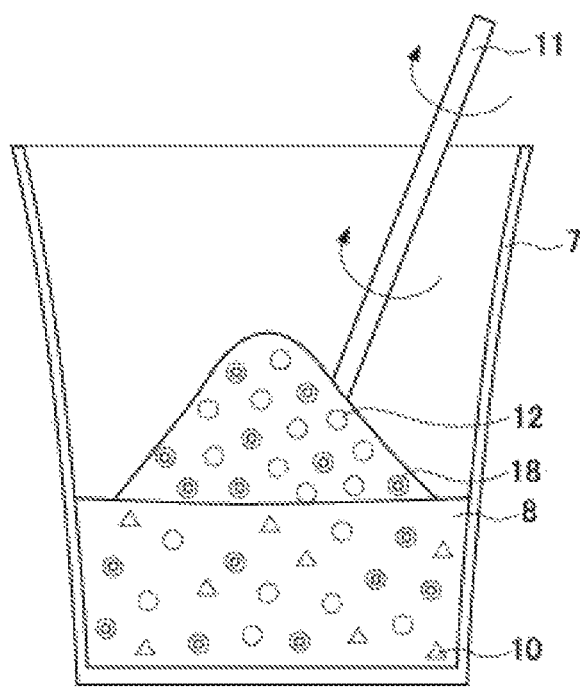
FIG. 13 is a sectional view depicting the preparation process of the present invention.
Figure 14:
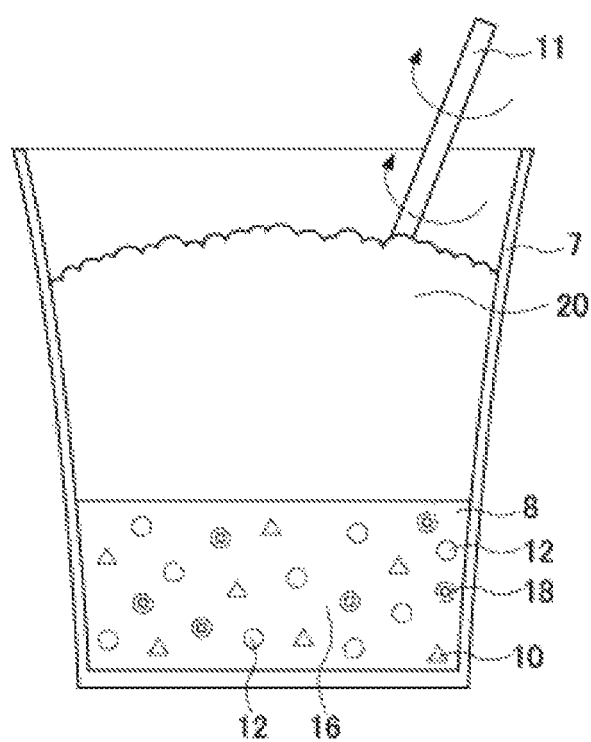
FIG. 14 is a sectional view depicting the preparation process of the present invention.

FIG. 12 illustrates a case in which a mineral supplementing agent for the living body according to the present invention is applied, in a small amount, to 22 (human skin) as 21 (liquid for improving blood circulation or a liquid for reducing harmful influences of electromagnetic waves and/or radioactive rays). A preparation method is illustrated in FIGS. 13 to 16. As depicted in FIG. 13, 7 (preparation tank) is charged with 40 L of 8 (vinegar), and then immediately with 20 kg of 10 (instant coffee), followed by stirring well. Thereafter, 7 (preparation tank) is charged with 20 kg of 18 (calcined ash of rice hulls) and 20 kg of 12 (fine particles of rice hulls), followed again by mixing the contents well. As a result, 18 (calcined ash of rice hulls) and 12 (fine particles of rice hulls) which are basic undergo an acid-base chemical reaction with 10 (instant coffee) and 8 (vinegar) which are acidic, and calcium carbonate contained in large amounts in 18 (calcined ash of rice hulls) and 12 (fine particles of rice hulls) is softened and decomposed. Then, carbonic acid is released from 18 (calcined ash of rice hulls) and 12 (fine particles of rice hulls), 20 (bubbles of a mixture generated upon mixing together of the calcined ash of rice hulls, the fine particles of rice hulls, the instant coffee, and vinegar) is rapidly generated, and the solution is expanded, as depicted in FIG. 14. Since the chemical reaction in this instance is vigorous and continuing, 20 (bubbles of a mixture generated upon mixing together of the calcined ash of rice hulls, the fine particles of rice hulls, the instant coffee, and vinegar) does not easily subside.

Figure 15:
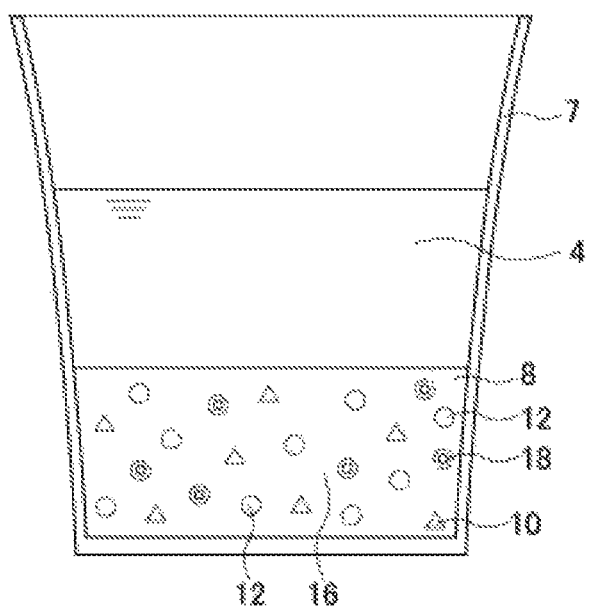
FIG. 15 is a sectional view depicting the preparation process of the present invention.
Figure 16:
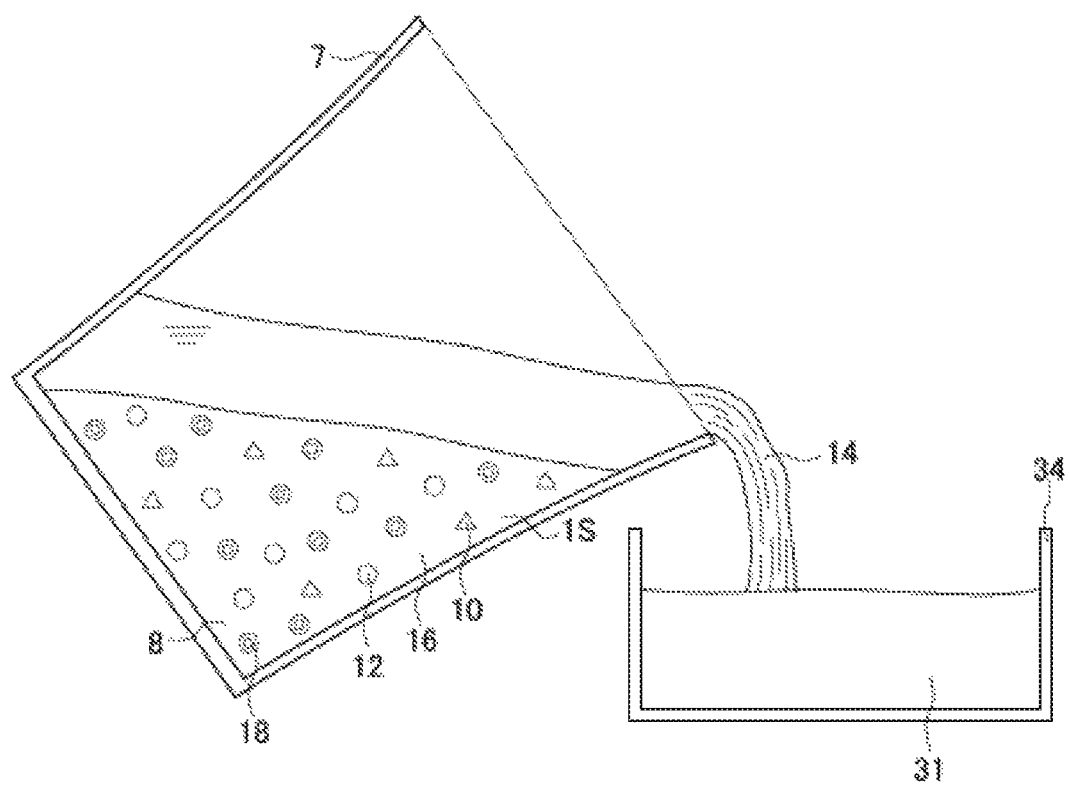
FIG. 16 is a sectional view depicting the preparation process of the present invention.

After standing still for at least eight hours, 20 L each of 8 (vinegar) is placed into 7 (preparation tank) six times. In this case, an operation of pouring 8 (vinegar) and stirring the contents well when the previous chemical reaction and the rapid bubbling have subsided is repeated. After a total of 120 L of 8 (vinegar) is entirely poured into 7 (preparation tank) and the contents therein are stirred, the contents are left to stand for at least three days until 20 (bubbles of a mixture generated upon mixing together of calcined ash of rice hulls, fine particles of rice hulls, instant coffee, and vinegar) subsides. When the chemical reaction has subsided and 20 (bubbles of the mixture generated upon mixing together of the calcined ash of rice hulls, the fine particles of rice hulls, the instant coffee, and vinegar) has disappeared, liquid component 14 (mineral solution to be used for the living body) and solid component 15 (dregs containing a mineral solution after making of the mineral solution to be used for the living body) are separated within 7 (preparation tank) as depicted in FIG. 15. As depicted in FIG. 16, this 7 (preparation tank) is inclined obliquely, only supernatant liquid component 14 (mineral solution to be used for the living body) is simply filtered, in such a manner that pasty solid component 15 (dregs containing the mineral solution after making of the mineral solution to be used for the living body) in the bottom does not mix in, to be used as 21 (liquid for improving blood circulation or a liquid for reducing harmful influences of electromagnetic waves and/or radioactive rays).

The resulting 21 (liquid for improving blood circulation or the liquid for reducing harmful influences of electromagnetic waves and/or radioactive rays) can be used for people of all age groups including babies. The undiluted solution may be directly applied, in a very small amount, to an apparently bad-conditioned part of the body, for example, parts of hands or feet where cold, an old wound, an eruption, or an ache is present, or the parietal region, the arm pit, the crotch, the back or the like.

Example 4

Figure 17:
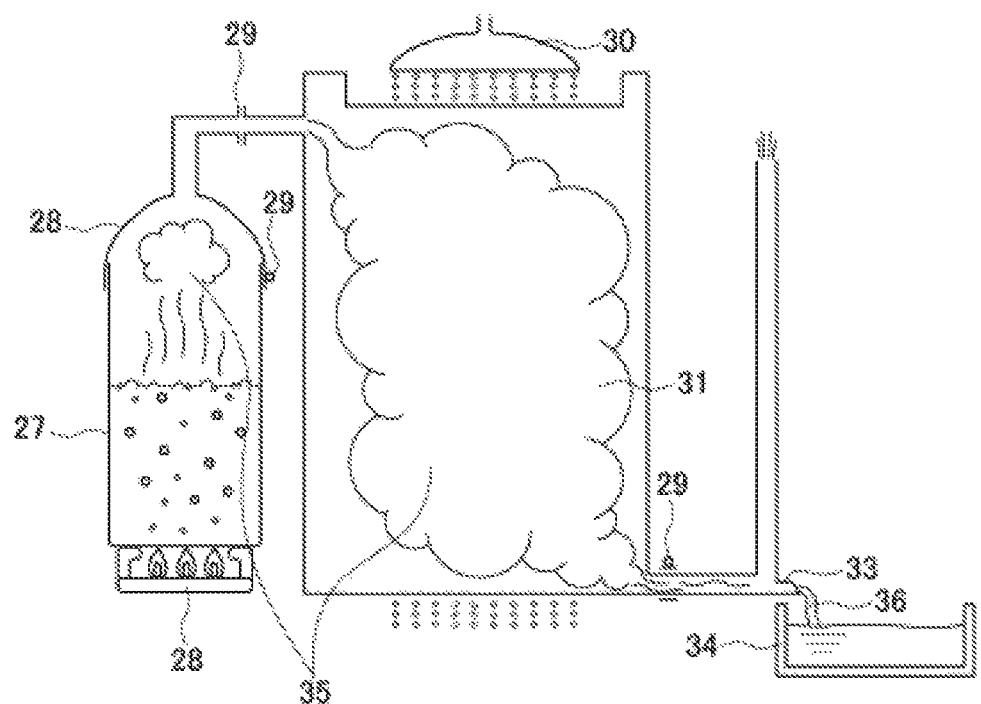
FIG. 17 is a sectional view depicting the preparation process of the present invention.

In the case where the mineral supplementing agent for the living body of the present invention is used as 24 (skin lotion), a preparation process depicted in FIG. 17 is added to the preparation process of FIGS. 4 to 7, FIGS. 8 to 11, and FIGS. 13 to 16. In the case of 14 (mineral solution to be used for the living body) prepared by use of the starting materials and preparation method depicted in the embodiment for making 1 (brown rice cooking seasoning liquid) described above, and also in the case of 14 (mineral solution to be used for the living body) prepared by use of the starting materials and preparation method depicted in an embodiment for making 21 (liquid for improving blood circulation or a liquid for reducing harmful influences of electromagnetic waves and/or radioactive rays) to be described later, the mineral solution becomes a substantially tasteless, odorless, and non-colored transparent mineral solution by being subjected to a distillation process conducted using 25 (distillation device) depicted in FIG. 17. When a small amount of the undiluted solution is taken by hand and directly applied to a face, a neck, a hand, or a foot, the undiluted solution is immediately absorbed in the bare skin, to make the skin smooth and translucent. This 24 (skin lotion) can be used as it is as a skin lotion, or may be used as a basic ingredient for making a skin lotion or related products.

Example 5

Figure 18:
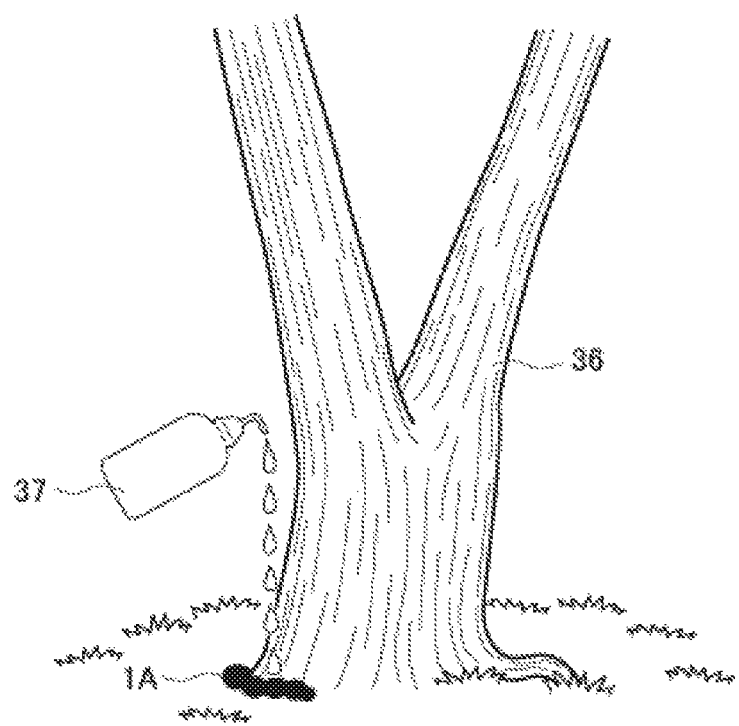
FIG. 18 is a plan view depicting an embodiment of the present invention.

FIG. 18 illustrates a case in which a mineral supplementing agent for the living body according to a third-named invention serves as 35 (a leaf surface spraying agent or fertilizer for plants). Each of 14 (mineral solution to be used for the living body) and 15 (dregs containing a mineral solution after making of the mineral solution to be used for the living body) in the case of being used as 1 (brown rice cooking seasoning liquid) of FIG. 3, 14 (mineral solution to be used for the living body) and 15 (dregs containing a mineral solution after making of the mineral solution to be used for the living body) in the case of being used as 21 (liquid for improving blood circulation or a liquid for reducing harmful influences of electromagnetic waves and/or radioactive rays) of FIG. 12, and further 15 (dregs containing a mineral solution after making of the mineral solution to be used for the living body) in the case of using the just-mentioned mineral solution as 24 (skin lotion), is effective when applied to plants as a leaf surface spraying agent or a fertilizer. In addition, 14 (mineral solution to be used for the living body) prepared in the following manner is also effective for plant bodies. Its preparation process is illustrated in FIGS. 19 to 22.

Figure 19:
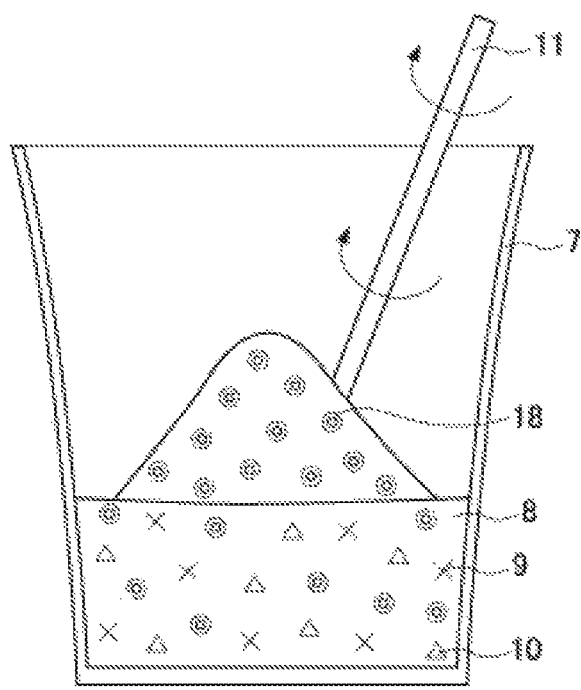
FIG. 19 is a sectional view depicting the preparation process of the present invention.
Figure 20:
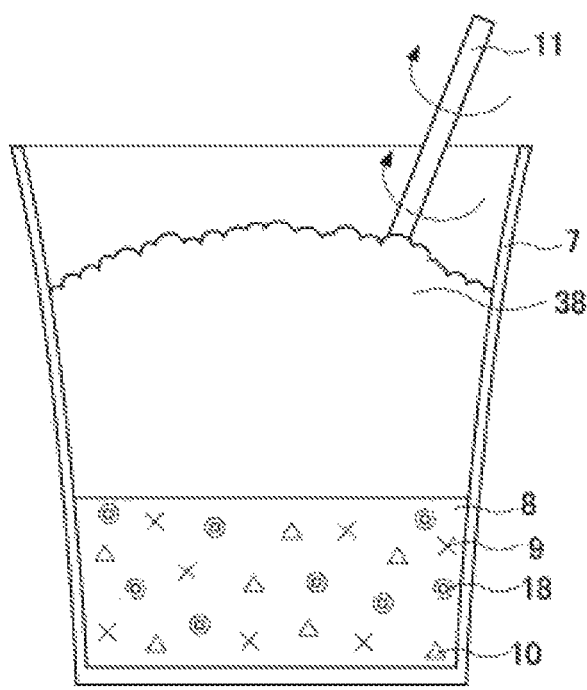
FIG. 20 is a sectional view depicting the preparation process of the present invention.
Figure 21:
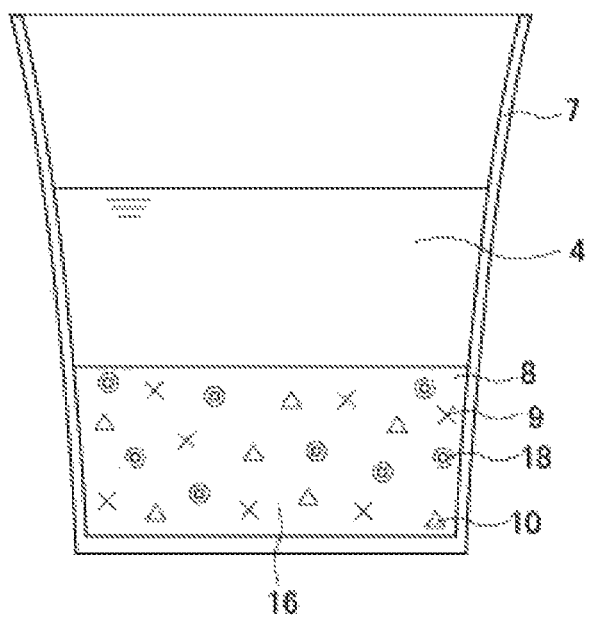
FIG. 21 is a sectional view depicting the preparation process of the present invention.

Specifically, as depicted in FIG. 19, 7 (preparation tank) is charged with 40 L of 8 (vinegar), and then immediately with 10 kg of 9 (garlic powder) and 10 kg of 10 (instant coffee), followed by stirring well. Thereafter, 7 (preparation tank) is charged with 40 kg of 18 (calcined ash of rice hulls), followed again by mixing well. As a result, 18 (calcined ash of rice hulls) which is basic undergoes an acid-base chemical reaction with 9 (garlic powder), 10 (instant coffee), and 8 (vinegar) which are acidic, and calcium carbonate contained in a large amount in 18 (calcined ash of rice hulls) is softened and decomposed. Then, carbonic acid is released from 18 (calcined ash of rice hulls), 38 (bubbles of a mixture generated upon mixing together of the calcined ash of rice hulls, the garlic powder, the instant coffee, and vinegar) is rapidly generated, and the solution is expanded, as depicted in FIG. 20. Although the chemical reaction in this instance is rapid and vigorous, it subsides in a short time, since stirring has preliminarily been conducted well.

Figure 22:
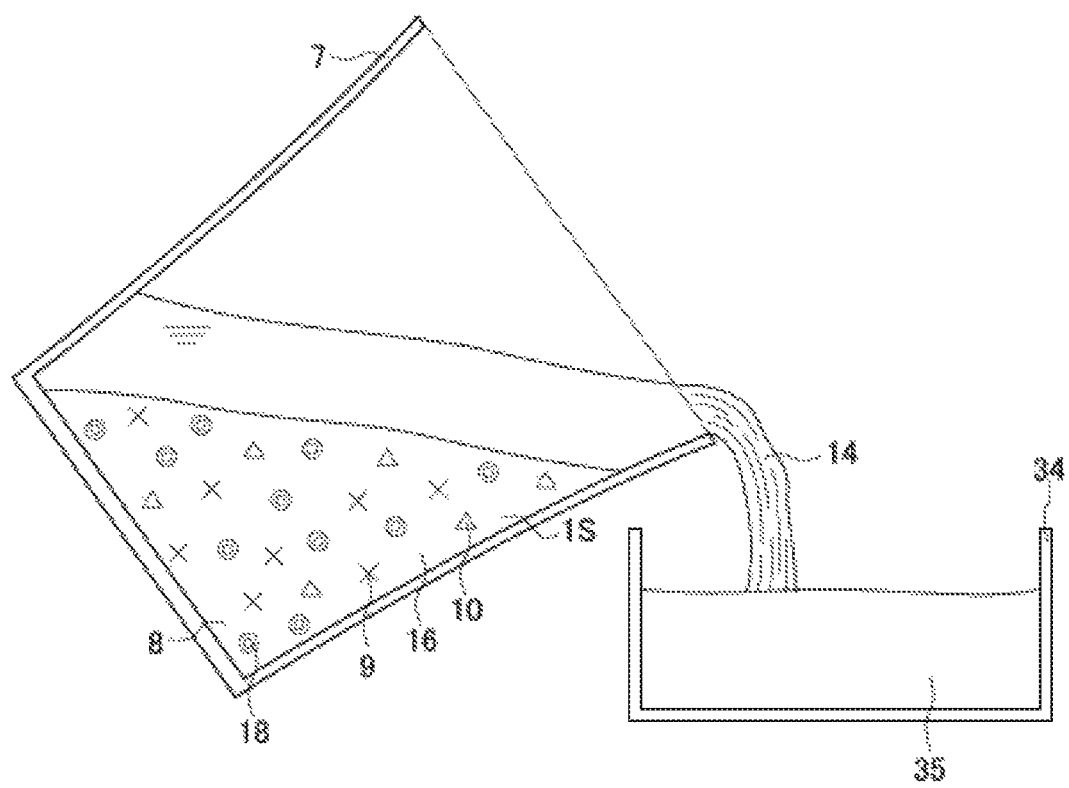
FIG. 22 is a sectional view depicting the preparation process of the present invention.
Figure 23:
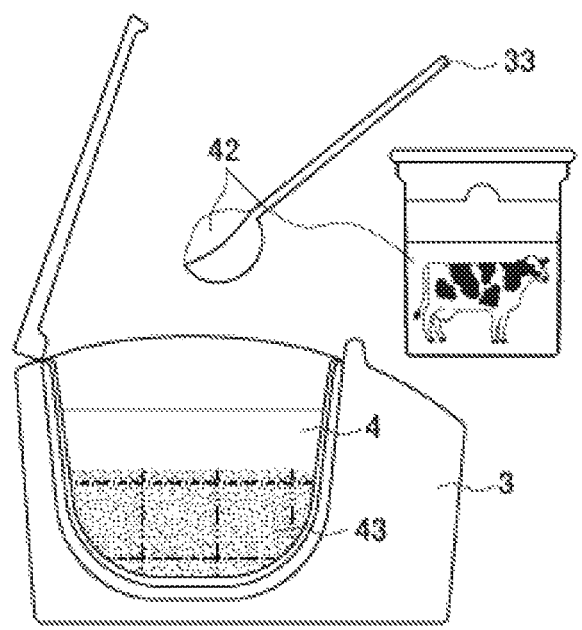
FIG. 23 is a plan view depicting a prior art.
Figure 24:
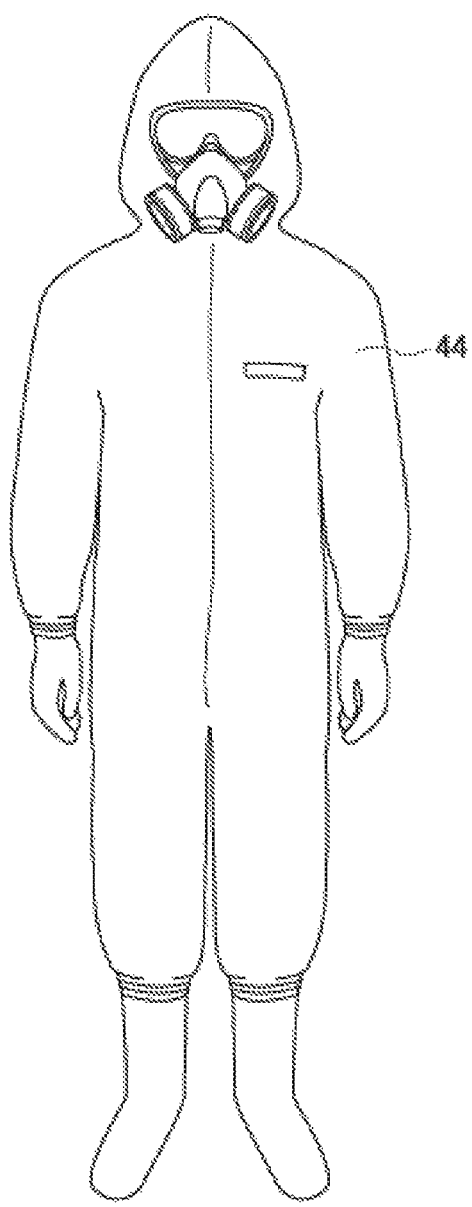
FIG. 24 is a plan view depicting a prior art.
Figure 25:
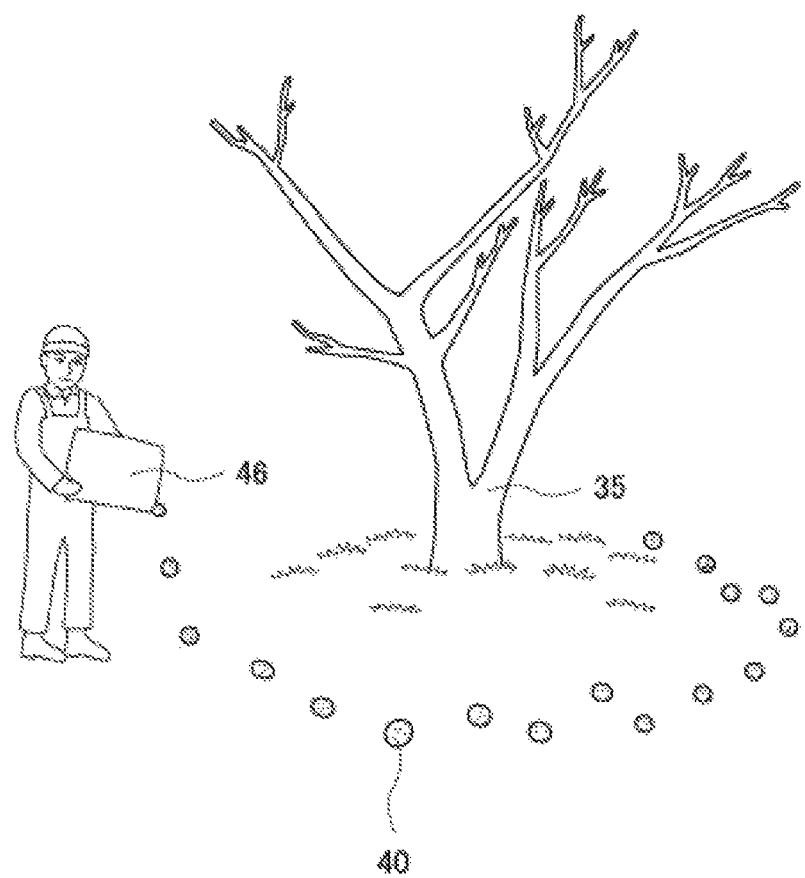
FIG. 25 is a plan view depicting a prior art.

Thereafter, also, 40 L each of 8 (vinegar) is placed into 7 (preparation tank) three times. In this instance, an operation of pouring 8 (vinegar) and stirring the contents well when the previous chemical reaction and the rapid bubbling have subsided is repeated. After a total of 120 L of 8 (vinegar) is entirely poured into 7 (preparation tank) and the contents therein are stirred, the contents are left to stand for two days. As a result, as depicted in FIG. 19, liquid component 14 (mineral solution to be used for the living body) and solid component 15 (dregs containing a mineral solution after making of the mineral solution to be used for the living body) are separated within 7 (preparation tank). As depicted in FIG. 22, this 7 (separation tank) is inclined obliquely, only supernatant liquid component 14 (mineral solution to be used for the living body) is simply filtered, in such a manner that pasty solid component 15 (dregs containing the seasoning liquid after making of the mineral solution to be used for the living body) in the bottom does not mix in, to be used as 39 (leaf surface spraying agent for plants). Further, pasty solid component 15 (dregs containing the mineral solution after making of the mineral solution to be used for the living body) in the bottom is used as 40 (fertilizer for plants).

14 (mineral solution to be used for the living body) which is prepared by each of the preparation methods and which includes only the liquid component is diluted and sprayed to leaf surfaces of plants as a leaf surface spraying agent, or is applied as it is directly to a near-root portion of the trunk of a tree as a fertilizer. In addition, pasty solid component 15 (dregs containing a mineral solution after making of the mineral solution to be used for the living body) which is prepared by each of the preparation methods and which contains the liquid component is applied as it is directly to a near-root portion of the trunk of a tree as a fertilizer, or placed in or on near-root soil as a fertilizer for crops.

The mineral supplementing agent of the present invention is not limited to the aforementioned uses. Specifically, the mineral supplementing agent can also be used as or in a seasoning, as or in a liquid for improving blood circulation in the human body, as or in a toothbrushing liquid or gargling liquid for the human body and the like.

Since the mineral supplementing agent of the present invention is produced by effectively utilizing as a mineral source the rice hulls which is ordinarily disposed of, it is possible to prepare a mineral supplementing agent at low cost.

In addition, since the rice hulls is rich in minerals such as potassium, calcium, iron, or phytic acid, the mineral supplementing agent of the present invention is capable of keep the human bodies and plants healthy.

Depending on the preparation method and use thereof, the mineral supplementing agent of the present invention can also produce the following effects.

In the case where the mineral supplementing agent of the present invention is used as a brown rice cooking seasoning liquid, the following effects are obtained. Firstly, brown rice cooking can be readily performed. In cooking brown rice, after lightly washing with water, a rice cooker is charged with a prescribed amount of water, and charged further with an additional amount of water which is 80 cc to 100 cc per 1 go of brown rice. Then, the brown rice cooking seasoning liquid of the present invention is added in an amount of 5 cc per 1 go of brown rice, thereafter, without mixing the contents, rice cooking is immediately started. Setting of the brown rice cooking using the rice cooker is finished in a shortest time of two minutes. Labor for preparing a meal in the morning or evening when the user is busy can be saved; thus, the brown rice cooking seasoning liquid suits to the life style of the modern people oriented toward labor saving.

Secondly, the cooked brown rice can be made comparable to cooked polished rice in appearance and taste. In the cases of the brown rice cooking seasoning liquids according to Citation List, coloration due to an instant coffee-originated coloring matter has been observed to some extent. However, in the case of the brown rice cooking seasoning liquid of the present invention, the cooked brown rice is closer to cooked polished rice in hue; therefore, a situation in which people accustomed to ordinarily eat cooked polished rice dislike cooked brown rice due only to the appearance of the latter can be avoided. In addition, the cooked brown rice itself gives a keen feeling of sweetness and umami, is soft, and stimulates the people's appetite.

Thirdly, not only the nutritional value of meals is enhanced because the brown rice itself can be made to be daily food, but also the use of the nutritional components of rice hulls and picked fruits as starting materials ensures that conventionally overlooked resources can be utilized as foodstuff for human diet. The brown rice cooking seasoning liquid supplements calcium, which is not contained in brown rice, and minerals such as iron, which may be excreted under the detoxifying effect of phytic acid contained in brown rice, whereby cooked brown rice can be made closer to a complete food.

Fourthly, since the calcined ash of rice hulls is used as a starting material of the brown rice cooking seasoning liquid of the present invention, an effect is added to the effect of phytic acid contained in brown rice on excretion of harmful substances and radioactive substances. The added effect lies in that potassium and calcium contained in the brown rice cooking seasoning liquid of the present invention inhibit radioactive substance cesium and radioactive substance strontium from being taken into the body, respectively. Due to the synergistic effect of these, harmful substances and radioactive substances are more strongly eliminated from the body, whereby internal radiation exposure due to radioactive substances can be alleviated.

Fifthly, "rice hulls" can be effectively utilized in the form of fine particles of rice hulls and calcined ash of rice hulls. Even in the case where marine resources of shell powders, fine particles of crusts, and fine particles of fish bones become hard to collect due to worsening of natural environments, the use of rice hulls in place of the marine resources makes it possible to prepare a brown rice cooking seasoning liquid of higher quality. This can be highly expected as a countermeasure against the expected difficulty of obtaining food. The rice hulls, which is extremely abundant in farm areas in autumn, is newly utilized for human life as foodstuff, instead of being disposed of. Thus, waste is avoided.

Sixthly, the grain hulls such as rice hulls is rich in minerals which keep the human bodies strong, and contains a large amount of phytic acid as compared to the brown rice. Therefore, the mineral supplementing agent of the present invention is capable of keep the human bodies and plants healthy.

In addition, in the case where the mineral supplementing agent of the present invention is used as a seasoning liquid, the following effects are produced.

Firstly, the mineral supplementing agent can be used in preparing a variety of side dishes, such as boiled foods, grilled dishes, soups, and noodle dipping sauces. When preparing daily food such as miso soup, stir-fried food, curry, and stew, the brown rice cooking seasoning liquid of the present invention may be put in an amount of approximately one teaspoon (5 cc) to approximately one tablespoon (15 cc) per 1 L of water, whereby the taste of the foodstuff is made most of, and a good taste and a high nutritional value are ensured.

Secondly, the time necessary for preparing a boiled food or a grilled dish can be shortened. Since thermal conduction efficiency is enhanced, transfer of heat through vegetables, meat, and fish is improved, so that umami is increased. This is well understood especially when onion is stir-fried; the time required for stir-frying onion until onion becomes light brown colored, by adding the brown rice cooking seasoning liquid in an amount of one tablespoon (15 cc) per one onion, is approximately half the corresponding time in the conventional way of cooking.

Thirdly, when a small amount of the brown rice cooking seasoning liquid is put into a fermented food such as pickles, fermented soybeans, and yoghurt, the fermentation is promoted and the umami is increased. When a pickle, fermented soybeans, or yoghurt to which the brown rice cooking seasoning liquid of the present invention has been added is eaten, the activity of enterobacteria is activated, and good bowl movement is ensured.

Fourthly, in the case where a small amount of the brown rice cooking seasoning liquid of the present invention is sprayed onto food when a pre-prepared cooked food such as fries and box meal is eaten, the oiliness of the fries is suppressed, to make the food easier to eat, and calcium and minerals originated in the brown rice cooking seasoning liquid can be taken into the body together with the food, so that the nutritional balance of the meal is enhanced.

Fifthly, when the brown rice cooking seasoning liquid is added to a retort-pouch food or an instant food, a new flavor can be added to the existing retort-pouch food or instant food, and the nutritional value of the food is enhanced. The brown rice cooking seasoning liquid of the present invention exhibits an effect of preventing osteoporosis and making the human body healthy. Therefore, when the brown rice cooking seasoning liquid is incorporated into space food for astronauts or meals for workers in decommissioning of a nuclear power plant, it is possible to make an indirect contribution to science.

In the case where the mineral supplementing agent of the present invention is used as a liquid for improving blood circulation, the following effects are obtained.

Firstly, when a small amount of the undiluted solution of the liquid for improving blood circulation of the present invention is applied to the arm pit, the crotch, or the sole of a foot of the human body, propagation of various bacteria can be prevented, and malodor and inflammation can be prevented.

Secondly, when a small amount of the undiluted solution of the liquid for improving blood circulation of the present invention is applied to a stiff part or aching part of the body, the solution is absorbed in the subcutaneous tissue, and, since the human body has predetermined element concentrations such as 1.5% of calcium and 1% of phosphorus, the metabolism for concentration control is promoted, whereby the stiffness or pain in the body can be alleviated.

Thirdly, when the undiluted solution of the liquid for improving blood circulation of the present invention is applied to the parietal region, occipital region, or temporal region before sleeping, fatigue in optic nerves, stiffening of the neck, shoulder or, back, and fatigue in hands or feet due to long-time use of a personal computer, tablet PC, or mobile phone can be mitigated, and harmful influences of electromagnetic waves can be reduced.

Fourthly, in the case where the liquid for improving blood circulation of the present invention is prepared by using calcined ash of grain hulls such as calcined ash of rice hulls, the concentration of potassium is increased, and an effect of inhibiting radioactive substance cesium from being taken into the body is obtained. Therefore, in the cases of persons living in an area of high radiation dose or persons working in decommissioning of a nuclear power plant, when the undiluted solution is applied to the skin every day or the persons wear underwear or clothing impregnated with the undiluted solution every day, external radiation damage can be alleviated. When children living in regions of high radiation dose or persons traveling to those regions consciously make habitual use of the liquid for improving blood circulation of the present invention, it will help clear up the potential anxiety or impatience. The mineral solution to be used for the living body of the present invention is also effective from the viewpoint of having no side effect.

Fifthly, the method of applying to the human skin the undiluted solution of the liquid for improving blood circulation of the present invention ensures that the effect of the solution can be exhibited at a part of the body where a bulky medical article such as a bandage or a supporter cannot be used.

Sixthly, when the undiluted solution of the liquid for improving blood circulation of the present invention is used by impregnating a bandage, a supporter or the like therewith, a stiff or ache in the body can be alleviated.

Seventhly, when the undiluted solution of the liquid for improving blood circulation of the present invention is used by applying a small amount of the solution to the hair, the hair is set firm to shape. The solution may be colored black, so that it can be used for concealing grey hair without producing any side effect.

In the case where the mineral supplementing agent of the present invention is used as a toothbrushing liquid or a gargling liquid, the following effects are obtained.

Firstly, toothbrushing and gargling can be performed by use of the mineral solution to be used for the living body of the present invention. A toothbrush on the market may be immersed in the undiluted solution of the mineral solution to be used for the living body of the present invention and toothbrushing may be conducted using it, or approximately 10 cc of the undiluted solution may be held in the mouth and gargling may be performed.

Secondly, by the ultrafine particulate (nanometer-sized) minerals, calcium, and neutralized organic acid, it is possible to remove dental plaque, fur on tongue, and various bacteria on the back of the throat which are hard to wash away, to remove viruses and influenza virus, and to restrain the propagation of them.

Thirdly, although the mineral solution to be used for the living body of the present invention has a smell and a taste derived from the organic matter, there is no side effect on the human body when toothbrushing or gargling is conducted using the mineral solution.

In the case where the mineral supplementing agent of the present invention is used as a skin lotion, the following effects are obtained.

Firstly, the mineral supplementing agent, as "a mineral solution which is to be used for the living body and which is free of coloration," has a combination of all the effects of the aforementioned brown rice cooking seasoning liquid and the aforementioned liquid for improving blood circulation. The freedom from coloration and from a strong odor is a favorable condition for easier use by the user.

Secondly, the ultrafine particulate (nanometer-sized) minerals, calcium, and neutralized organic acid are more finely divided through the distillation process, whereby the osmotic pressure of the solution is enhanced and easier absorption into the bare skin is ensured.

Thirdly, when the undiluted solution of the skin lotion of the present invention is applied directly to a poor blood circulation part, an aching part or a rough dry skin part of the body on a daily basis, blood circulation is improved, ache is mitigated, the rough dry skin is cured, and the skin is conditioned, without any coloration. As compared with the liquid for improving blood circulation that has not been subjected to distillation, the undiluted solution of the skin lotion is stronger in the ability to remove pain from the body, but is weaker in the capability to inhibit adsorption of radioactive substance cesium.

Fourthly, when the undiluted solution of the skin lotion of the present invention is continuously applied directly to an eruption, tumor, or induration worrying the user on a daily basis, the eruption, tumor, or induration is gradually reduced in size.

In the case where the mineral supplementing agent of the present invention is used as a leaf surface spraying agent or a fertilizer for plants, the following effects are obtained.

Firstly, when the mineral supplementing agent is diluted with water and sprayed onto leaf surfaces or is placed in or on soil as a fertilizer, healthy and firm growth of plants is promoted, so that crops such as cut flowers, vegetables, and fruits keep well for a longer time, and color and luster of plants can be increased. In addition, since the convection of body fluid in plant bodies is promoted, the resistance of plant bodies against cold or heat is increased, and the ability to grow flowers or fruits can be enhanced.

Secondly, in the case where the undiluted solution is dripped or sprayed onto a near-root portion of the trunk of a fruit tree, in the season of bud growth or flower blossom, the flower buds grow firmly and large, and good flowers can be caused to bloom. In addition, frost damage due to frost can be alleviated. In the season of fruit growth or fruit finishing, umami or sugar content can be increased, and the fruits can be finished to be large, firm, and good in color and luster.

Thirdly, in the case where the mineral solution to be used for the living body of the present invention is used as a leaf surface spraying agent or a fertilizer for plants to thereby supplement minerals and trace-amount elements, the ultra-fine particulate (nanometer-sized) minerals, calcium, and neutralized organic acid are supplied in the form of being easily absorbed in the plant bodies and in microorganisms in the ground and small animals in the ground that are coexisting in the plant growth environments, and, therefore, the producer's working efficiency can be enhanced. In other words, high-quality crops can be harvested in larger amounts, so that a cycle of rising income and rising profits can be established.

Fourthly, since the leaf surface spraying agent and fertilizer are each of 100% organic matter, and, therefore, they have no side effect, and build up a non-burdening relationship with not only plant bodies but also the global ecosystem.

INDUSTRIAL APPLICABILITY

The mineral supplementing agent of the present invention can be used by itself as a seasoning, a supplement, a cosmetic or the like, or can be used by mixing it in an existing seasoning, supplement, cosmetic or the like.

Further, the mineral supplementing agent of the present invention may be used as a handy oral cleaning agent by incorporating it into throat candy, chewing gum, or Jintan (a mouth refrigerant), or may be mixed in water or a feed to be given to animals or fish, such as to serve as a nutrient with which the animals or fish can be bred without depending much on drugs.

REFERENCE SIGNS LIST

1 Brown rice cooking seasoning liquid
2 Brown rice
3 Rice cooker
4 Water
5 Measuring spoon
6 Bottle filled with brown rice cooking seasoning liquid
7 Preparation tank
8 Vinegar
9 Garlic powder
10 Instant coffee
11 Stirring rod
12 Fine particles of rice hulls
13 Bubbles of mixture generated upon mixing together of fine particles of rice hulls, garlic powder, instant coffee, and vinegar
14 Mineral solution to be used for living body
15 Dregs containing mineral solution after making of mineral solution to be used for living body
16 Powder of freeze-dried vinegar
17 Extract obtained by processing orange fruit into pasty form
18 Calcined ash of rice hulls
19 Bubbles of mixture generated upon mixing together of calcined ash of rice hulls, fine particles of rice hulls, garlic powder, instant coffee, powder of freeze-dried vinegar, extract obtained by processing orange fruit into pasty form, and vinegar
20 Bubbles of mixture generated upon mixing together of calcined ash of rice hulls, fine particles of rice hulls, instant coffee, and vinegar
21 Liquid for improving blood circulation or liquid for reducing harmful influences of electromagnetic waves and/or radioactive rays
22 Human skin
23 Bottle filled with liquid for improving blood circulation or liquid for reducing harmful influences of electromagnetic waves and/or radioactive rays
24 Skin lotion
25 Distillation device 26 Gas range
27 Boiling furnace
28 Attachment for boiling furnace and cooling oven
29 Metal fixture
30 Shower for flow of cooling water
31 Cooling oven
32 Hot air exhaust and liquid collection device
33 Distillate outlet
34 Liquid vessel
35 Leaf surface spraying agent or fertilizer for plants
36 Fruit tree
37 Bottle filled with mineral solution for plants
38 Bubbles of mixture generated upon mixing together of calcined ash of rice hulls, garlic powder, instant coffee, and vinegar
39 Leaf surface spraying agent for plants
40 Fertilizer for plants
41 Brown rice after immersed in water overnight
42 Yoghurt
43 Spoon
44 Protective clothing and person in protective clothing
45 Fertilizer and person placing fertilizer

The invention claimed is:

1. A method of producing a mineral supplementing agent capable of being administered to a human body or a plant, the method characterized by comprising:
   a first charging step of charging a vessel with part of a prescribed amount of vinegar;
   a second charging step of charging the vessel, which has been charged with the vinegar, with a garlic, an instant coffee, a vinegar, and optionally a fruit;
   a third charging step of charging the vessel, which has been subjected to the second charging step, with a particulate grain hull fine particles of rice hulls, a charred product thereof, and a calcined ash thereof, and mixing the contents of the vessel;
   a fourth charging step of adding the rest of the prescribed amount of vinegar to the vessel which has been subjected to the third charging step, while stirring the contents of the vessel concurrently with the addition; and
   an extraction step of separating a liquid component and a solid component in the vessel, after the fourth charging step, and extracting the separated liquid component as the mineral solution supplementing agent comprising a phytic acid;
obtaining the solid component left upon the extraction step, for use as a seasoning liquid for humans and as a fertilizer for plants.

2. The method of preparing a mineral supplementing agent according to claim 1,
   wherein the garlic in a powdery form, the instant coffee in a powdery form, the vinegar in a powdery form, and a dried powder of a juice of the fruit is used in the second charging step.

3. The method of preparing a mineral supplementing agent according to claim 1, further comprising:
   a distillation step of further distilling the mineral solution extracted in the extraction step, to produce a substantially tasteless, odorless, and non-colored solution.

4. A mineral supplementing agent characterized by comprising a phytic acid and capable of being administered to a human body or a plant, characterized by comprising:
   vinegar;
   a powdered nano-scale garlic, powdered nano-scale instant coffee, powdered nano-scale vinegar, and a dried powder of a juice of a fruit; and
   a nanometer-order particulate grain hull fine particles of rice hulls, a charred product thereof, and a calcined ash thereof.

* * * * *